United States Patent
Conolly et al.

(10) Patent No.: US 12,072,400 B2
(45) Date of Patent: Aug. 27, 2024

(54) STRONGLY-INTERACTING MAGNETIC PARTICLE IMAGING

(71) Applicants: The Regents of the University of California, Oakland, CA (US); University of Florida Research Foundation, Incorporated, Gainesville, FL (US)

(72) Inventors: Steven Conolly, Walnut Creek, CA (US); Carlos Rinaldi, Gainesville, FL (US); Bo Zheng, Seattle, WA (US); Prashant Chandrasekharan, Berkeley, CA (US); Daniel Hensley, Emeryville, CA (US); Shehaab Savliwala, Gainesville, FL (US); Zhi Wei Tay, Singapore (SG); Rohan Deepak Dhavalikar, Hillsboro, OR (US)

(73) Assignees: The Regents of the University of California, Oakland, CA (US); University of Florida Research Foundation, Incorporated, Gainesville, FL (US)

( * ) Notice: Subject to any disclaimer, the term of this patent is extended or adjusted under 35 U.S.C. 154(b) by 14 days.

(21) Appl. No.: 17/629,301

(22) PCT Filed: Jul. 23, 2020

(86) PCT No.: PCT/US2020/043307
§ 371 (c)(1),
(2) Date: Jan. 21, 2022

(87) PCT Pub. No.: WO2021/016473
PCT Pub. Date: Jan. 28, 2021

(65) Prior Publication Data
US 2022/0260655 A1    Aug. 18, 2022

Related U.S. Application Data

(60) Provisional application No. 62/877,601, filed on Jul. 23, 2019.

(51) Int. Cl.
*G01R 33/12* (2006.01)
*A61B 5/0515* (2021.01)

(52) U.S. Cl.
CPC ........ *G01R 33/1276* (2013.01); *A61B 5/0515* (2013.01)

(58) Field of Classification Search
CPC ................... G01R 33/1276; A61B 5/0515
See application file for complete search history.

(56) References Cited

U.S. PATENT DOCUMENTS

| | | | |
|---|---|---|---|
| 9,846,206 B2* | 12/2017 | Graziani | A61B 5/0515 |
| 10,048,224 B2* | 8/2018 | Goodwill | G01R 33/0213 |
| 2016/0216353 A1* | 7/2016 | Heinen | G01R 33/4808 |

OTHER PUBLICATIONS

Tay Zhi Wei: "Novel Scanning Strategies in x-Space Magnetic Particle Imaging for Improved Imaging Performance and Theranostic Applications", Jan. 1, 2018 (Jan. 1, 2018), pp. 1-279, XP093058157, ISBN: 979-8-6625-0325-0; Retrieved from the Internet: URL:https://www.proquest.com/dissertations-theses/novel-scanning-strategies-x-space-magnetic/docview/2436914820/se-2 [retrieved on Jun. 27, 2023].

(Continued)

*Primary Examiner* — Gregory H Curran
(74) *Attorney, Agent, or Firm* — Venable LLP; Henry J. Daley

(57) ABSTRACT

A magnetic particle imaging system that includes a magnetic field generating system with at least one magnet and providing a gradient magnetic field within an observation region such that the gradient magnetic field has a dynamic field-free region (FFR) for an object under observation having strongly-interacting magnetic particles distributed (Continued)

therein. The magnetic field generating system also includes a drive field and a slow shift field that dynamically shifts the FFR across a field of view (FOV) within the observation region, where the trajectory of the drive field accommodates for a coercivity of the strongly-interacting magnetic particles by ensuring that the particles in the FOV are saturated to a full coercivity field prior to traversing to an opposite-polarity of coercivity. The magnetic particle imaging system also includes a detection system proximate the observation region and configured to detect a signal from the strongly-interacting magnetic particles. The magnetic particle imaging system further includes signal processor in communication with the detection system, configured to receive and process the detected signal to remove a coercivity shift due to the coercivity of the strongly-interacting magnetic particles, and convert the processed detection signal into an image of the strongly-interacting magnetic particles.

20 Claims, 19 Drawing Sheets

(56) References Cited

OTHER PUBLICATIONS

Kornig, Andre et al., "Probing the mechanical properties of magnetosome chains in living magnetotactic bacteria". In: Nano Lett., (2014), 14.8, pp. 4653-4659.

Kandasamy et al., "Functionalized hydrophilic super paramagnetic iron oxide nanoparticles for magnetic fluid hyperthermia application in liver cancer treatment", ACS Omega, Apr. 10, 2018, vol. 3, pp. 3991-4005.

Rahmer et al., "Signal encoding in magnetic particle imaging: properties of the system function", BMC Medical Imaging, (2009), vol. 9, No. 4, (21 pages).

Ferguson et al., "Magnetic particle imaging with tailored iron oxide nanoparticle tracers", IEEE Trans Med Imaging [Internet]. (May 2015), vol. 34, No. 5, pp. 1077-1084. Available from: http://dx.doi.org/10.1109/TMI.2014.2375065 Pmcid: PMC4428902.

Tay et al., "The Relaxation Wall: Experimental Limits to Improving MPI Spatial Resolution by Increasing Nanoparticle Core size", Biomed Phys Eng Express, (Jun. 2017), vol. 3, No. 3, (21 pages).

Them, "On magnetic dipole-dipole interactions of nanoparticles in Magnetic Particle Imaging", Phys Med Biol [Internet], (May 3, 2017), No. 62, pp. 5623-5639; Available from: http://dx.doi.org/10.1088/1361-6560/aa70ca PMID: 28467324.

Lu et al., "Multi-channel Acquisition for Isotropic Resolution in Magnetic Particle Imaging". In: IEEE Trans. Med. Imaging, (Sep. 2018), vol. 37, No. 9, 1989-1998.

Ziemian et al., "Optimization of iron oxide tracer synthesis for magnetic particle imaging", Nanomaterials, (2018), vol. 8, No. 180, pp. 1-13, published Mar. 21, 2018.

Deissler et al., "Dependence of Brownian and N'eel relaxation times on magnetic field strength," Med. Phys. (Jan. 2014), vol. 41, No. 1, p. 012301-1 012301-12.

Finer et al., "Single myosin molecule mechanics: piconewton forces and nanometre steps" Nature, (Mar. 10, 1994), vol. 368, pp. 113-119.

* cited by examiner

STRONGLY-INTERACTING MAGNETIC PARTICLE IMAGING

CROSS-REFERENCE TO RELATED APPLICATION

The application is a U.S. National Stage Application under 35 U.S.C. § 371 of PCT/US2020/043307, filed Jul. 23, 2020, which claims priority to U.S. Provisional Application No. 62/877,601 filed Jul. 23, 2019, the entire contents of which are hereby incorporated by reference.

This invention was made with Government support under Grant Number R21 EB018453, awarded by the National Institutes of Health. The Government has certain rights in the invention.

BACKGROUND

Technical Field

The field of the currently claimed embodiments of this invention relates to magnetic particle imaging (MPI) devices and methods, and more specifically to strongly-interacting magnetic particle imaging.

SUMMARY

A strongly interacting magnetic particle imaging system according to an embodiment of the current invention includes a magnetic field generating system that includes at least one magnet, the magnetic field generating system providing a gradient magnetic field within an observation region of the magnetic particle imaging system such that the gradient magnetic field will have a dynamic field-free region (FFR) for an object under observation having strongly-interacting magnetic particles distributed therein. The magnetic field generating system also includes a drive field plus a slow shift field that dynamically shifts the FFR across a field of view (FOV) or partial FOV (pFOV) within the observation region, where a trajectory of the drive field accommodates for a coercivity of the strongly-interacting magnetic particles by ensuring that the strongly-interacting magnetic particles in the FOV or pFOV are saturated to a full coercivity field substantially immediately prior to traversing to an opposite-polarity of coercivity. The strongly interacting magnetic particle imaging system also includes a detection system arranged proximate the observation region, where the detection system is configured to detect an induction signal from the strongly-interacting magnetic particles to provide a detection signal. The strongly interacting magnetic particle imaging system further includes a signal processor in communication with the detection system, where the processor is configured to receive the detection signal from the detection system, process the detection signal to remove a coercivity shift due to the coercivity of the strongly-interacting magnetic particles, and convert the processed detection signal into an image of the strongly-interacting magnetic particles.

A strongly-interacting magnetic particle tracer according to an embodiment of the current invention includes multiple superparamagnetic nanoparticles, where the superparamagnetic particles are arranged to have a surface-to-surface separation between nearest-neighbor particles that does not exceed ten times the radius of the particles. In the presence of an applied magnetic field whose amplitude exceeds a coercivity threshold, the superparamagnetic nanoparticles manifest a measurable level of coercivity.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 1:
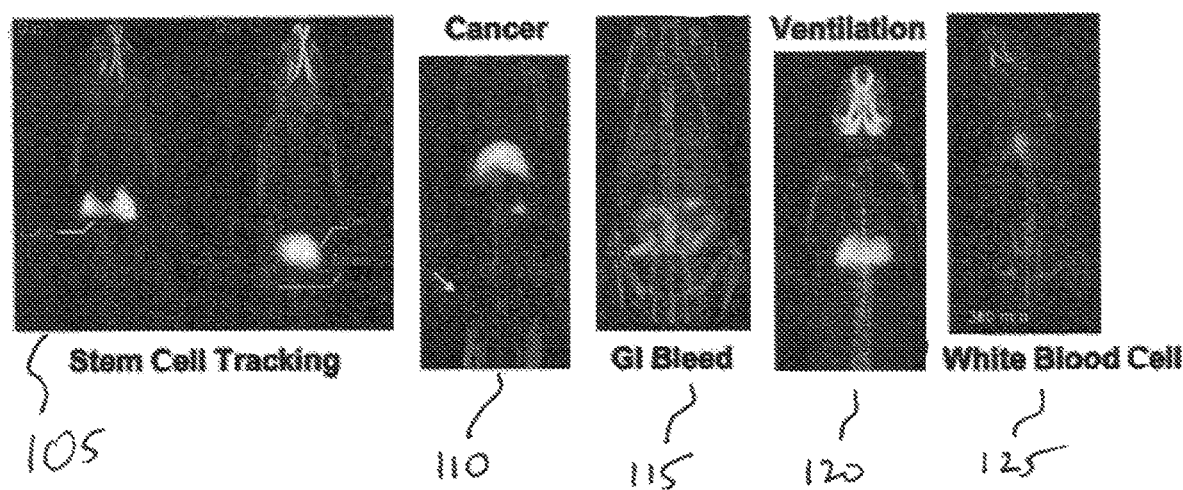
FIG. 1 shows first-in-animal in vivo MPI experiments including tracking cell therapies, early-stage detection of cancer, gastrointestinal bleeds, pulmonary embolisms, and immunotherapies.

Magnetic Particle Imaging (MPI) is a biomedical imaging modality with zero radiation, near-ideal contrast, sensitivity, and depth penetration. MPI provides a zero-radiation complement to Nuclear Medicine and Radiation Therapy and provides a noninvasive replacement for several multi-billion-dollar Nuclear Medicine applications. FIG. 1 shows example images from first-in-animal in vivo MPI experiments for several such applications. As illustrated in FIG. 1, MPI can be used for stem cell tracking (105), early-stage detection of cancer 110, gastro-intestinal (GI) bleeds 115, pulmonary embolism 120, and immunotherapies 125. Other potential applications include strokes, cardiovascular disease, and neurological disease. Each of these and other clinical and biomedical applications have potentially large clinical impact once an ideal MPI iron oxide nanoparticle tracer is developed.

MPI can be a powerful tool for early-stage cancer detection. The best predictor of long-term cancer survival remains early-stage detection. As an example, cancer.gov shows that detection of breast cancer at stage 1 has over 95% survival rates, whereas detection at stage 4 has far more dismal 25% survival rates. While 60% of breast cancer is already diagnosed at the earliest stage, it would be preferable if 90%+ were diagnosed at the earliest stage. However, only 16% of lung cancer is diagnosed at the earliest stage.

Figure 2:
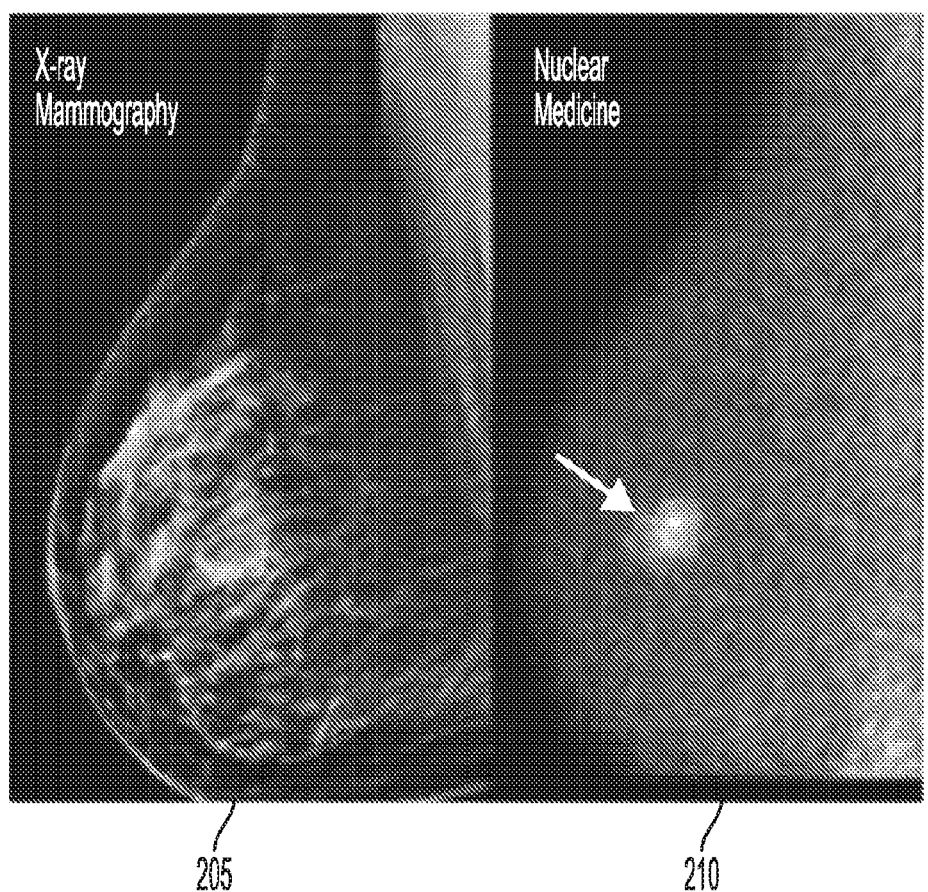
FIG. 2 illustrates a comparison of X-ray mammography and nuclear medicine sestamibi Tc99m scintigraphy for a patient with dense breast tissue.

As the comparison in FIG. 2 illustrates, scintigraphy can detect a breast cancer long before it is visible in a mammogram from a woman with radiologically dense breast tissue. The breast tumor is completely missed in the mammogram 205 but is clearly evident in the nuclear medicine scan 210. However, this preferred nuclear medicine cancer imaging modality cannot be used for early-stage breast cancer detection due to excess cost and radiation. Instead, physicians must rely on X-ray mammography, which has inferior contrast in the 47% of women with radiologically dense breast tissue.

In contrast, MPI would not suffer from high cost or radiation. Indeed, it has zero radiation, and comparable cost to X-ray mammography. Also, MPI would have no trouble seeing through dense breast tissue. MPI penetrates any tissue, including bone, lungs, and dense breast tissue. Hence, MPI may provide a zero-radiation, early-stage cancer screening tool for cancer screening.

Figure 3:
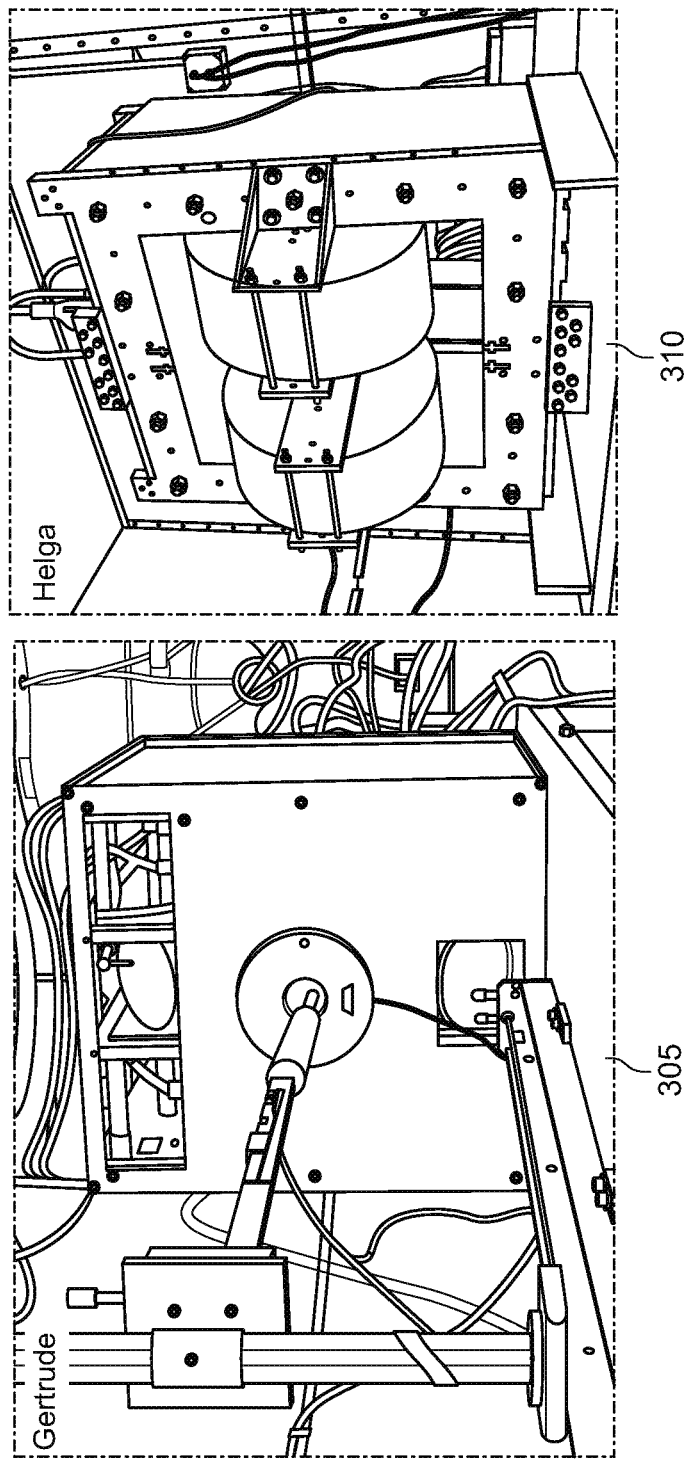
FIG. 3 illustrates examples of custom hardware MPI scanners.

MPI scans and MPI therapeutic treatments cannot be performed in a Magnetic Resonance Imaging (MRI) scanner. Accordingly, customized scanner hardware, pulse sequences, and reconstruction software are required. The MPI murine scanners 305 and 310 illustrated in FIG. 3 each weigh 2000 pounds, and use cooling and RF shielding. With nanoscale physics and chemistry techniques, MPI-tailored superparamagnetic iron oxide (SPIO) nanoparticles are developed, with which the scanners can detect labeled cells in minutes, with high contrast and spatial resolution.

U.S. Pat. Nos. 8,847,592 and 8,884,617, and U.S. Publication No. 2019/0079149, all describe earlier work in MPI and are incorporated by reference herein in their entirety.

Figure 4:
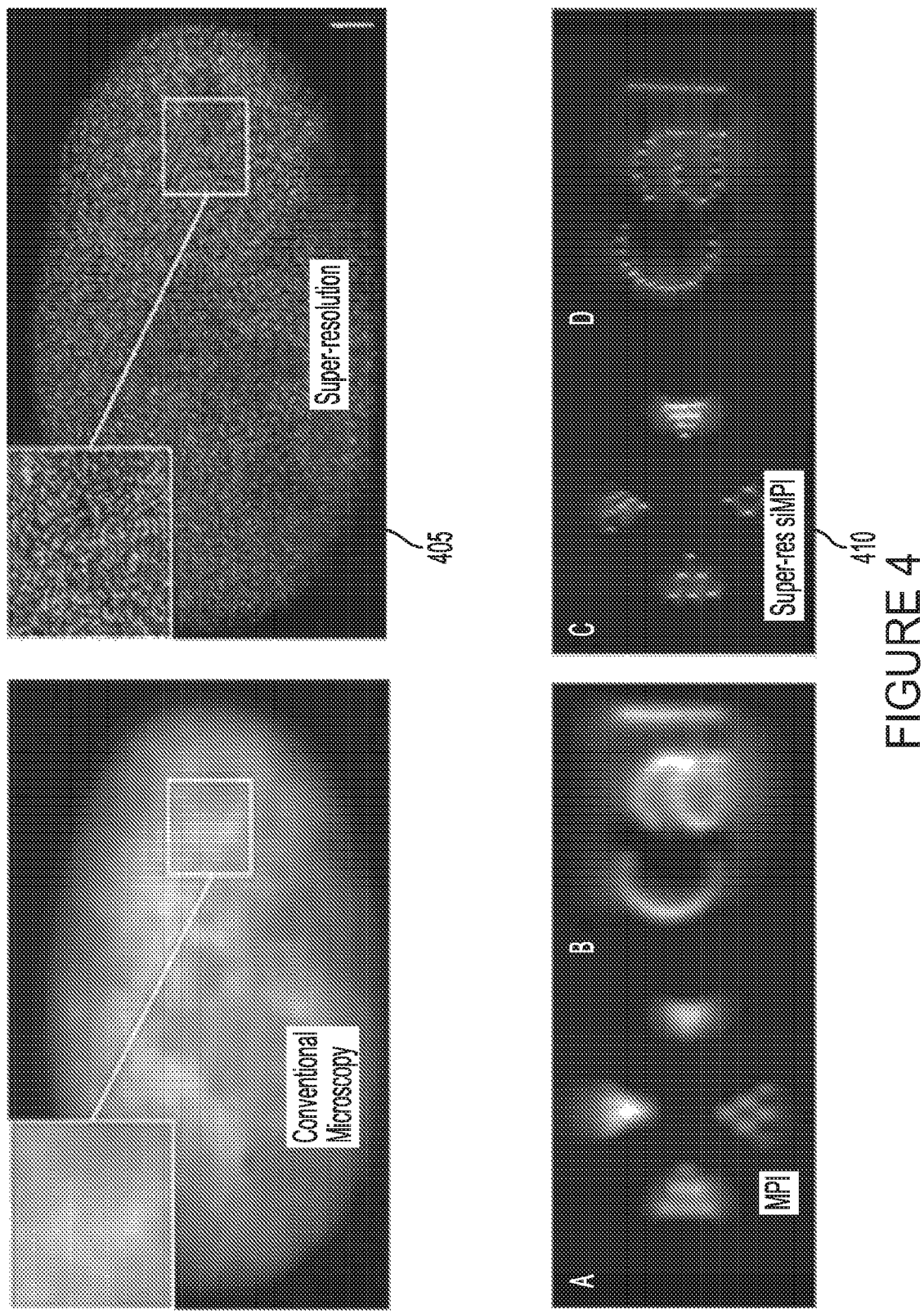
FIG. 4 illustrates the resolution gain of super-resolution microscopy, and super-resolution strongly-interacting MPI (siMPI).

As discussed above, MPI is a promising new tracer modality with zero attenuation in tissue, near-ideal contrast and sensitivity, and an excellent safety profile. The spatial resolution of MPI is currently the modality's only weak technical attribute which holds back the development of human MPI scanners. Recently, proof-of-concept studies were demonstrated for an MPI modality, referred to herein as strongly-interacting magnetic particle imaging (siMPI) that enables a super-resolution breakthrough. Preliminary work indicates siMPI can provide more than a 6-fold improvement in every dimension of space spatial resolution and 37-fold increase in sensitivity. This resolution boost is reminiscent of super-resolution microscopy. FIG. 4 illustrates the resolution gain 405 of super-resolution microscopy, in comparison to super-resolution strongly-interacting MPI (siMPI) 410. Once optimized, this approach could reduce the cost of a human-sized MPI scanner by 100-fold. A safe, super-resolution version of MPI could remove the major bottleneck in the field of clinical MPI.

MPI relies on super-paramagnetic iron oxide (SPIO) tracers, which can also double as localized heating agents. Currently, using state-of-the-art MPI gradients and SPIOs, measurements of 1 mm spatial resolution are possible in small animal scanners. This is a straightforward consequence of the resolution of the currently best-available SPIOs (roughly 7-mT magnetic transition width, called full width half max, FWHM) and the strength of today's strongest gradients (7 T/m). To derive spatial resolution, the SPIO magnetic field FWHM is divided by the gradient strength, e.g., 7 mT/(7T/m)=1 mm FWHM resolution. It would be a major advance in the field of MPI if 0.7 mT FWHM magnetic field resolution were achieved, allowing for 10-fold higher native spatial resolution without increasing gradient strength (which is already near the practical limits). In the examples below, compelling experimental evidence is provided that one embodiment of the invention could achieve this 10-fold improvement.

A significant hardware cost in both MRI and MPI scanners is the strong gradient coil. To date, no one has yet made a successful clinical MPI scanner partially due to the cost of scaling up the gradient from preclinical to clinical size. Ideally, 1 mm resolution must be achieved in future clinical MPI scanners, to compete with X-ray CT and MRI. To accomplish this feat, a 7000 mT/m gradient is needed. While this is technically achievable at human scales (using expensive superconducting magnets), it would be much more cost effective and improve human safety (dB/dt and Specific Absorption Rate (SAR)) if the required gradient could be reduced by an order of magnitude, to 700 mT/m (or weaker) gradients for human MPI.

Fortunately, siMPI could achieve precisely this situation. Because gradient hardware scales roughly quadratically with strength, a ten-fold reduction in gradient strength would translate to nearly a 100-fold reduction in clinical MPI gradient cost, as well as 10-fold mitigation in human safety concerns (dB/dt and SAR).

Table 1 shows a comparison of spatial resolution and field gradients with MRI, conventional MPI, and siMPI. Note that with this situation, MPI would be comparable to the MRI field, where the resolution (and gradient strength) are 10-fold stronger in preclinical scanners. With a potential 10-fold improvement in FWHM resolution, the human MPI gradient could be reduced 10-fold, which could in turn reduce human MPI scanner cost by 100-fold and improve biosafety.

TABLE 1

Comparison of spatial resolution and field gradients
with MRI, conventional MPI and siMPI.

| Modality | SPIO FWHM | Gradient | Resolution |
| --- | --- | --- | --- |
| MRI preclinical | NA | 400 mT/m | 100 microns |
| MRI clinical | NA | 40 mT/m | 1 mm |
| Standard MPI preclinical | 7 mT | 7000 mT/m | 1 mm |
| Standard MPI clinical (putative) | 7 mT | 7000 mT/m | 1 mm |
| siMPI preclinical | 0.7 mT | 7000 mT/m | 100 microns |
| siMPI clinical | 0.7 mT | 700 mT/m | 1 mm |

Both current MPI reconstruction algorithms—referred to as x-space and harmonic space—rely on a non-interacting physics model of SPIOs. The assumption of non-interaction means that the field felt by one SPIO from adjacent SPIOs is negligible compared to the applied field. However, recent relaxometer and MPI scanner images have shown experimental evidence that certain SPIOs show dramatically improved resolution, and signal to noise ratio (SNR), but only when (a) at a concentration above a crucial threshold and (b) only when the drive field amplitudes exceed a certain level of coercivity. Also, these experiments show clear evidence of ferromagnetic hysteresis behavior, including remanence and coercivity. These observations are stark departures from standard non-interacting Langevin physics.

Evidence from dozens of scientific experiments suggest that the underlying reason for the starkly different behavior is that individual SPIOs aggregate under a magnetic field to form a magnetic chain. The chains exhibit both ferromagnetic and super-paramagnetic behaviors. Because this behavior is only seen at high local concentrations (where chain formation by magnetic attraction is feasible even given viscous drag), this new MPI approach is referred to herein as Strongly-Interacting Magnetic Particle Imaging (siMPI). With optimization, this approach could revolutionize the resolution and sensitivity of MPI, and perhaps enable clinical MPI.

Herein a novel, compact, and intuitive MPI physics model is presented for how strongly interacting SPIOs may respond to an applied magnetic field. The mathematical physics predicts dramatically higher resolution and SNR, compared to noninteracting Langevin physics, in accordance with siMPI experimental data. This siMPI analysis provides modifications to x-space analysis and image reconstruction methods and predicts dramatic resolution improvements as well as SNR boosts. It also prescribes scanning waveform to accommodate dB/dt and SAR limitations as well as the hysteresis inherent to siMPI.

According to an embodiment of the invention, four elements contribute to the success of siMPI: strongly interacting SPIOs at high local concentration but safe bulk concentration; high-drag encapsulation to prevent motion in a strong gradient; drive field waveforms that exceed the coercivity of the chain; and an image reconstruction algorithm that removes the coercive offsets.

Experimentally, chain formation in a magnetic field is observed only at high enough local concentrations to ensure that the attractive dipole fields are strong enough to exceed viscous drag and thereby pull SPIOs together. However, to minimize toxicity, it is desired to minimize overall nanoparticle concentration. This combination of high local concentration and low bulk concentration can be achieved with encapsulation in micelles, liposomes, PRINT encapsulations, etc.

In a low-frequency homogenous drive field, individual SPIOs are attracted to each other. The attractive force scales with the inverse fourth power of the SPIO separation distance. In conventional MPI, the SPIOs are separated by more than roughly 10 diameters, and hence the attractive force is reduced by more than 10,000-fold. This intuition matches experiments where siMPI behavior is seen only if the local concentration exceeds a critical threshold. However, bulk concentrations need to be minimized in order to minimize toxicity. Both goals may be achieved by encapsulating SPIOs, allowing high local concentration and safe bulk concentrations. There are many established ways to ensure this encapsulation safely, including encapsulation in liposomes, micelles, PRINT particles, etc. Nanoscale fabrication techniques can also be employed to print chains of SPIOs on discs. This behavior may even be seen in rod-shaped SPIOs. Also, 5 to 25 superparamagnetic nanoparticles can be tethered with soft ligands to accommodate chain formation in an applied magnetic field. This architecture has various names, including "snakes" and "nanostrings." See https://www.pnas.org/content/116/15/7543. Superparamagnetic nanoparticles can also be prepared such that two adjacent superparamagnetic particle cores are separated by non-magnetic, low-surface-charge shell coatings, where the thickness of each of the non-magnetic shell coatings does not exceed 10 nm.

Also, it is necessary to ensure the encapsulations have high enough drag to not move in a strong 10T/m gradient because this could be dangerous and ruin image resolution. This is analogous to the "peloton effect" made famous in in bicycle races, where the chain feels reduced viscous drag (per SPIO) and then magnetomotive forces would overcome viscous drag, causing motion that could be dangerous. Conventional, non-interacting SPIOs are not observed to move in a strong field gradient, like the exit of an MRI scanner (where there is a gradient stronger than 1 T/m). Hence, several design options are explored to permit chain formation while limiting magnetomotive force as to render the siMPI chains safe in humans and animals. For example, in some embodiments of the invention, the superparamagnetic nanoparticles may be enclosed in a carrier capsule that has an outer surface that enhances viscous drag, for example, PEG or Dextran.

It is already known that individual SPIOs do not move in a strong field gradient because viscous forces exceed magnetomotive forces. A chain could permit a reduction in viscous drag/SPIO, much like a peloton in bicycle racing. Preventing magnetomotive drift will be a crucial safety constraint. The length of the chain is limited and the viscous drag of the encapsulation (micelle, liposome, PRINT encapsulation, etc.) is increased in some embodiments of the invention by using large hydrodynamic coatings (e.g., 100 nm Dextran or PEG shells). This will be a far less significant concern for siMPI particles that are attached to relatively large bodies (1-microns+) prior to injecting (e.g., Stem Cells, White Blood Cells, Red Blood Cells, Macroaggregated Albumin, Dendritic Cells, etc.) because the viscous drag from the large bodies will thwart the Magnetomotive force.

The dynamic ensemble magnetization of the strongly interacting SPIOs resembles a magnetization curve where there is a coercivity, corresponding to the instantaneous field required to reverse the magnetization of the collection of strongly interacting SPIOs. Here, this threshold field value is referred to as the coercivity of the chain. In some embodiments of the invention, drive field waveforms are used that exceed the coercivity of the chain. Such drive field waveforms have an amplitude and frequency that exceed a minimum drive field amplitude and a minimum drive field frequency required to exceed the coercivity. Because siMPI chains exhibit hysteresis (with both coercivity and remanence) it is essential that the drive waveform amplitudes exceed the coercivity threshold. Otherwise, non-siMPI behavior is observed. Care must be taken to ensure FDA safety (dB/dt and heating SAR) while allowing for siMPI.

Finally, an image reconstruction algorithm is used in some embodiments of the invention that accounts for coercivity of siMPI chains. Using x-space reconstruction methods or system matrix reconstruction methods, it is essential that the drive waveform amplitudes exceed the coercivity threshold and that the coercivity-shift is removed from the image reconstruction method. Methods in some embodiments may include isotropic resolution and equalization of any residual non-siMPI behavior.

According to some embodiments of the invention, a zipper sequence scanning trajectory is used where the partial field of view (pFOV) is identical to the full field of view (FOV) and the scanning frequency is roughly 1 kHz (or 0.5 ms per directional scan). This scanning sequence provides nearly all the SNR and spatial resolution of 25 kHz scanning but with greatly mitigated scanner cost and greatly mitigated FDA electromagnetic safety constraints, allowing for a full FOV 2D scan in perhaps 1 ms. The FDA safety constraints are included in a recent paper, https://ieeexplore.ieee.org/document/6510534, incorporated herein by reference in its entirety. FDA safety constraints set limits on dB/dt for peripheral nerve stimulation (roughly must keep dB/dt<20 T/s) and patient heating specific absorption rate (SAR) and require minimizing "particle SAR" (pSAR or Magnetic Fluid Hyperthermia) because the hysteresis curve is traversed only once for each particle during a scan.

According to an embodiment of the invention, a strongly-interacting magnetic particle imaging system includes a magnetic field generating system comprising at least one magnet. The magnetic field generating system provides a dynamic or static gradient magnetic field within an observation region of the magnetic particle imaging system such that the gradient magnetic field will have a dynamic field-free region (FFR) for an object under observation having strongly-interacting magnetic particles distributed therein. The dynamic gradient magnetic field can be provided by a pair of time gradient coils (with two separate drive amplifiers). Alternatively, the gradient magnetic field may be a static gradient field that is combined with a dynamic homogeneous drive field plus a (slow) homogeneous shift field. The vector sum of these three fields shifts the zero-field point of the gradient across space.

In addition to the static or dynamic gradient magnetic field, the magnetic field generating system provides a drive field plus a slow shift field that dynamically shifts the FFR across a field of view (FOV) or partial FOV (pFOV) within the observation region, where a trajectory of the drive field accommodates for a coercivity of the strongly-interacting magnetic particles by ensuring that the strongly-interacting magnetic particles in the FOV or pFOV are saturated to a full coercivity field substantially immediately prior to traversing to an opposite-polarity of coercivity.

The strongly-interacting magnetic particle imaging system includes a detection system arranged proximate the observation region, the detection system being configured to detect an induction signal from the strongly-interacting magnetic particles to provide a detection signal. The strongly-interacting magnetic particle imaging system includes a signal processor in communication with the detection system, wherein the processor is configured to: receive the detection signal from the detection system; process the detection signal to remove a coercivity shift due to the coercivity of the strongly-interacting magnetic particles; and convert the processed detection signal into an image of the strongly-interacting magnetic particles.

According to an embodiment of the present invention, the pulse sequence or acquisition trajectory and/or reconstruction method is configured to detect both conventional magnetic particle imaging signals and strongly-interacting magnetic particle imaging signals simultaneously. Signal from strongly-interacting MPI is shifted spatially from the FFR by the coercive threshold while signal from conventional-MPI occurs at FFR point, therefore the imaging strategy is designed to ensure that the raw data (unprocessed time-domain detection signal from detection system) has clear separation of the two signal peaks in time.

According to an embodiment of the present invention, the system is frequency-flexible and amplitude-flexible to accommodate a range of coercive thresholds, chain formation, or chain crumble time constants, from a range of tracer/nanoparticles designs or from in vivo changes to the nanoparticles. Changes in coercive thresholds or chain formation relaxation time constant or chain crumbling relaxation time constants can be used to measure in vivo events, or also used for multiplexed 'color' contrast where different nanoparticle tracers have different activation characteristics that are sequentially/simultaneously probed by the system as per 'multi-color' detection.

According to an embodiment of the present invention, the drive field or other excitation components are configured to actively breakdown the strongly-interacting magnetic particle imaging tracers from their chain configuration to suppress siMPI detection signal and thereby provide biochemical or physiologic contrast. Various metrics such as the chain formation time, chain crumbling time, coercivity threshold, frequency cut off time-to-breakdown or frequency-to-breakdown can be assessed from the detected ion signal and may provide a method to provide an imaging method with the contrast from the biochemical or physiologic local microenvironment including viscosity. The recovery of the siMPI detection signal after this 'spoiler' pulse a delay time can also be assessed in some embodiments to probe the above-mentioned microenvironment or simply as a method to generate MPI signal contrast.

According to an embodiment of the invention, a strongly-interacting magnetic particle tracer includes a plurality of superparamagnetic nanoparticles. The plurality of superparamagnetic particles are arranged to have a surface-to-surface separation between nearest-neighbor particles that does not exceed ten times a radius of the particles. In the presence of an applied magnetic field whose amplitude exceeds a coercivity threshold, the plurality of superparamagnetic nanoparticle manifests a measurable level of coercivity.

According to an embodiment of the invention, the chains include five to 100 superparamagnetic nanoparticles. However, this number could be much larger as siMPI could work with larger/longer chains, especially for cell tracking, MAA-labeled tracers (Ventilation/Perfusion) or other "inertial" imaging applications. The chains may be applied to two categories of applications where the safety constraints (specifically magnetomotive drift) differ significantly. To date, there are no applications of MPI outside these two categories. 1) Angiography: here only the "naked" tracer is injected into a vein and it must be short (5-50 SPIOs) to prevent magnetic field drift. 2) Labeled Tracer: this is common with tracking something big (cells are about 20 microns, so much bigger than SPIOs. Macro-aggregated albumin (MAA) is about 50 microns and so these will provide heavy inertia that will prevent motion in a field gradient. Hence, much longer siMPI chains may be used (e.g., 1000 SPIOs). According to an embodiment of the invention, the chains include 100 to 500 superparamagnetic nanoparticles. According to another embodiment of the invention, the chains include 500 to 1000 superparamagnetic nanoparticles.

According to an embodiment of the invention, the carrier capsule includes a liquid disposed in the carrier capsule, where the liquid's viscosity is changeable and sensitive to the external microenvironment that the capsule is in. That is, the nanocarrier capsule gel sensors contains a liquid whose viscosity is designed to be reversibly and monotonically sensitive to pH, pO2, glucose concentration, or other microenvironment, physiologic or metabolic factors. For example, a pulse sequence with chain formation time contrast could provide contrast in the MPI scan based on local blood pO2 concentration (provided the nanocapsule gel had viscosity sensitive specifically to pO2, pH or Glucose concentration) and this image information could reveal sites of metabolic pathophysiology including cancers, heart disease, stroke, inflammation, infection or other disease processes.

According to an embodiment of the invention, the carrier capsule's diameter varies according to microenvironmental factors or stimuli. For example, pH-sensing microfibers that contract in acidic pH to shrink the carrier capsule diameter and alter siMPI chain formation. This may manifest as a method as a switch-like pH sensor through presence or absence of siMPI detection signal at the coercive threshold point.

According to an embodiment of the invention, the magnetic field is applied to form chains during particle synthesis. A solid matrix is allowed to set around the particle chain to ensure a close-contact chain structure even after removal of the magnetic field. The subsequent particle when applied to imaging does not require magnetic field for chain formation but would require a coercive field applied as per MPI imaging system in claim A1 to induce magnetization reversal and generate a strongly-interacting MPI signal.

According to an embodiment of the invention, the capsule or the solid matrix around the nanoparticles is degraded by specific agents in vivo. The time-to-degrade is measured by loss of siMPI signal from release of particles from the solid matrix or capsule, and can serve as a sensor of various in vivo activity rates, such as enzymatic rates in vivo. Alternatively, this can be used to measure pH such as acidic local microenvironment in a tumor or pO2 or glucose concentration for tracers designed to be chemically responsive to these metabolites. This is one method to generate local pathologic contrast (in tumors, strokes, or cardiovascular disease, etc.) may degrade the tracer solid matrix or outer capsule faster than in healthy tissue.

According to an embodiment of the invention, the plurality of superparamagnetic nanoparticles are attached to disparate points of a macromolecular structure or molecular structure, such that changes in molecular or macromolecular formation bring the disparate points of the structure into close proximity, enabling the superparamagnetic nanoparticles to interact to produce siMPI signal upon excitation by a strongly-interacting magnetic particle imaging system. The concept is similar to the basic concept of FRET, where the new fluorescence emission peak is highly-dependent and sensitive to the proximity of two chromo/fluorophores, however, superparamagnetic nanoparticles are used in place of fluorophores and the operating scale of the 'magnetic FRET' would be proportionally larger to the size difference between nanoparticles and FRET chromo/fluorophores. While this may limit the application to proteins larger in size to nanoparticles (10-25 nm), this is applicable to larger proteins such as Titin which is greater than 1 micron in length as a way to image folding in vivo and at-depth. Applications may not be limited to proteins, but also other synthetic chemical structures in vivo.

According to an embodiment of the invention, the plurality of superparamagnetic nanoparticles have individual shells (typically oleic acid shell) that are configured to change thickness in response to a local metabolic indicator (e.g., pO2, pH, [glucose], [insulin]) such that swelling of the coatings produces visible changes in the siMPI signal. Most noticeably, this should alter the coercivity, which could then be measured on a pixel-by-pixel basis and used to create molecular contrast from the local environment.

According to an embodiment of the invention, the plurality of superparamagnetic nanoparticles are attached to tethers to ligands that bind to the surface of the cell. In vivo, the concentrations are too dilute to form a chain for siMPI. However, when the ligands bind to the cell surface, the nanoparticles-on-tethers are now close enough, raising the local concentration, to produce siMPI signal, thus indirectly imaging cell surface binding in vivo and at depth.

According to an embodiment of the invention, the plurality of superparamagnetic nanoparticles are attached to tethers to ligands are taken up by the cell. In vivo, the concentrations are too dilute to form a chain for SiMPI. However, when the ligands are taken up by the cell and these endocytosis vesicles coalesce into a larger internal vesicle, the nanoparticles from separate vesicles are brought together, raising the local concentration, to produce SiMPI signal, thus indirectly imaging cell uptake in vivo and at depth.

According to an embodiment of the invention, the nanoparticle size or nanoparticle coating thickness is varied to generate different coercive threshold for siMPI detection signal, resulting in different "effective" colors for multiplex sensing. For example, an injected mixture of 15 nm nanoparticles (encapsulated) and 20 nm nanoparticles (encapsulated) will produce siMPI detection signal at different coercive thresholds, enabling 'multi-color' imaging or facile filtering of one or the other by adjustment of the MPI drive amplitude—insufficient amplitude to hit coercivity will imply no signal from that particle.

According to an embodiment of the invention, different particles are enclosed in different liposomes, and detection of the mixing of different-particle liposomes in a cell (e.g., macrophage, stem cell, WBC, etc.), is used for detection of a cellular event in vivo. For example, siMPI signal from 15-nm or 20-nm populations may differ from a mixture of 15 and 20 nm particles as a result of liposomes fusing within a macrophage. This may be detected by changes in coercive threshold or chain formation or chain 'crumble' time.

Herein, the term "substantially immediately" is intended to mean sufficiently quickly to maintain the strong interactions between the strongly-interacting magnetic particles. According to some embodiments of the invention, substantially immediately means within 10 ms or less. According to some embodiments of the invention, substantially immediately means within 1 ms or less.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described Examples The following describes some particular embodiments of the current invention in more detail; however, the general concepts of the current invention are not to be limited to these particular examples.

Modeling MPI Physics for Strongly Interacting Magnetic Nanoparticles: SIMPI

Magnetic Particle Imaging (MPI) is a promising new tracer modality with zero attenuation in tissue, high contrast and sensitivity, and an excellent safety profile. However, the spatial resolution of MPI is currently around 1 mm in small animal scanners. Especially considering the cost and complexity tradeoffs when scaling up MPI scanning systems to human size, this resolution must be improved significantly to mitigate cost and magnetic safety (dB/dt and SAR) of human clinical MPI. Specifically, a ten-fold improvement in FWHM resolution SPIO could reduce the total costs of a human nearly one-hundred-fold.

All current MPI methods—including x-space and harmonic space methods-rely on noninteracting physics model of SPIOs. That is, the field felt by one SPIO from adjacent SPIOs is modeled to be completely negligible compared to the applied field.

However, recent relaxometer and MPI scanner images have shown experimental evidence that certain SPIOs show dramatically improved resolution, noticeable hysteresis and SNR, in clear defiance of standard non-interacting Langevin physics. It seems likely that these new SPIOs are strongly interacting. Hence, this new MPI approach is termed siMPI (Strongly Interacting Magnetic Particle Imaging). The approach is to greatly amplify the local applied magnetic field, and thereby dramatically improve spatial resolution and SNR.

Here a compact, intuitive MPI physics model is presented for how strongly interacting SPIOs will respond to an applied magnetic field in some embodiments of the invention. The mathematical physics predicts dramatically different behavior compared to noninteracting Langevin physics. This SIMPI analysis provides modifications to x-space analysis and image reconstruction methods and predicts dramatic resolution improvements as well as SNR boosts. It also prescribes scanning waveform to accommodate dB/dt and SAR limitations as well as the hysteresis inherent to SIMPI.

Observations on Interacting SPIOs for MPI

Recent relaxometer and MPI imaging experiments have demonstrated anomalously high spatial resolution using NPs with 20 kHz MPI. Three different NPs have shown roughly 10-fold better MPI resolution than previously best SPIOs (LS-008). The first data published on magnetic NPs showed incredibly fine resolution (under 1 mT FWHM) with standard 20 kHz drive field excitation provided the peak drive field amplitude exceeded a coercivity threshold. Several drastic changes in behavior were observed from traditional MPI SPIOs, including:

Hysteresis: The spins show a noticeable coercive field, meaning the spins would flip at $H=\pm H_c$ (instead of at $H=0$), but only after being fully "latched" at the opposite sign. This behavior violates many tenets of X-space MPI theory, in that noninteracting SPIOs always flip at zero field, and noninteracting SPIOs respond to the current instantaneous magnetic field, regardless of prior history.

Concentration Latching: High resolution behavior only occurs when the NPs are packaged in an emulsion at a concentration over a critical threshold. Below that concentration, the SPIOs showed significantly worse spatial resolution. This is a blatant violation of LSI behavior, where resolution is completely independent of concentration. This may be due to chain formation, where SPIO field gradients are strong enough to attract when SPIOs are close enough to each other.

Artifacts in 3D Scanner: Both AWR and a 2D PSF image were both very promising for high resolution emulsion imaging. However, 2D complex phantom images failed to show improved spatial resolution. This is presumably due to magnetomotive motion of the large emulsions, which may have been tens or hundreds of microns in size.

The central idea of the Interacting SPIO physics model, inspired by older concepts with chained SPIOs, is that a tight chain of SPIOs could amplify the local magnetic field, thereby improving spatial resolution. The interacting NMP model described Positive Feedback with a saturation device, which is a common model in Control Theory and Communications Engineering. This has similarity to a Schmitt trigger, which is a "comparator circuit with hysteresis implemented by applying positive feedback to the noninverting input of a comparator or differential amplifier." Simulators (in Python and MATLAB) were written to simulate the interacting SPIO model, which have a few unknown parameters. The simulations predicted the observed experiments very well, as shown in this document.

This document outlines the mathematical physics analysis of the new Strongly Interacting Magnetic NP (siMNP) model of some embodiments of the invention. This SIMNP model helps to explain the observed anomalous fine resolution and coercivity. More importantly, the siMNP model prompts several experimentally verifiable predictions.

Introduction to Strongly Interacting Magnetic Nanoparticles

A fundamental assumption in MPI is that the tracer concentration is so low that the dipole field from neighboring SPIOs is trivial compared to the applied magnetic field. Of course, the magnetic dipole field falls off cubically with distance, z, asymptotically as $(a/z)^3$, where a is the radius of the SPIO. So, if SPIOs are spaced apart by 10 core-radii, then the field contribution felt at one SPIO falls off by the factor $1/10^3 = 1/1000$. Even with an intense 600 mT saturation field in the neighboring SPIO, at a distance of 10a, the field is only 0.6 mT, which is small compared to a typical field saturation, about 6 mT. At low concentrations, the SPIOs are simply too far apart to "feel" the magnetic field induced by their neighbors. Under this "noninteracting" assumption, the SPIO responds only to the applied magnetic field. This is a core assumption in x-space papers and other literature.

However, heterostructures can certainly be designed that link SPIOs in a tight chain, akin to magnetosomes in a magnetic bacterium. Also, there is considerable literature on observations of spontaneous chain formation in the presence of a magnetic field (Wilson et al. 2009). Clearly, the noninteracting assumption is no longer valid if the center-to-center SPIO separation in the chain is less than ~ 10 radii (10a). Chain formation is not a stable process, and chains are common in aggregation and magnetomotive force becomes evident with larger SPIOs.

Recognizing the need for high local concentration at low bulk concentrations, emulsions were created with high local concentration and AWR measurements showed remarkably sharp FWHMs, using conventional 20 kHz excitation, but with high amplitudes. SPIOs have been packaged at high concentration in micelles and liposomes; this could be far more powerful and reliable than the emulsions process. In addition, "nanocarriers" can also be designed that allow for safe, bulk concentrations (well below 2 mM [Fe]) with high concentration within the nanocarriers. The noninteracting assumption is essential to reassure contrast agent companies (e.g., Bayer, Advanced Magnetics who make Ferumoxytol, LodeSpin Labs, etc.) of the safety considerations for SPIO nanoparticles. Once chain formation starts, this process is likely to continue unabated, until all free SPIOs are linked into the chain. Considering that viscous drag scales linearly with radius a, and magnetomotive force scales cubically ($a^3$), it is thought that only small, noninteracting SPIOs will remain stationary in a magnetic field gradient. Larger SPIOs, akin to the professional bicycle racing "peloton effect" would feel relatively weaker viscous drag compared to magnetomotive force. This bulk motion could be dangerous to a patient and could also destroy image resolution. Until recently, there was no reason to embrace interacting SPIO chains. More thoughts on how to prevent these serious safety concerns are discussed below.

Because interacting SPIOs do not follow the standard x-space physics, a new physical model is urgently needed. The MPI imaging equations must be re-derived, including spatial resolution, SAR, dB/dt, and bandwidth.

Adiabatic Physics Model for Short Chains of Interacting SPIOs

Each SPIO will obey Langevin physics, which describes the competition between magnetic and thermal (noise) torques. But in an interacting chain, both the applied field and the field induced by the chain must be included. One SPIO at the center of a chain may be arbitrarily picked to model. For magnetomotive safety, the chains will likely need to be made as short as feasible, perhaps 3-9 SPIOs in length. The SPIOs at the ends of the chains may exhibit slightly different magnetic behavior, but this should be OK, and could even be essential to make magnetomotive effects safe.

The total field felt by a single SPIO is:

$$H_{total} = H_1 + \alpha M \quad (1)$$

Here the dimensionless term $\alpha$ models the net contribution from all the SPIOs in the chain, including the falloff in field with distance. Since the falloff is cubic with distance, the dominant contribution will come from the two adjacent SPIOs. Suppose a short chain of SPIOs are all touching (no separation, z=2a) so $(a/z)^3 \approx 1/8$. Including only the two adjacent SPIOs, the field contribution from two fully saturated adjacent SPIOs could reach $\mu_0 M_{sat} \approx 600$ mT×2/8=150 mT, which is much stronger than typical saturation fields (about 6 mT). Clearly, the induced field from the chain cannot be neglected.

The magnetization induced in a single SPIO, neglecting relaxation (adiabatic model) can be written as an iterative (transcendental) equation:

$$M = M_{sat} \mathcal{L}([H_1 + \alpha M]/H_{sat}) \quad (2)$$

It helps to rewrite this Langevin equation with normalized fields. This allows for a single, universal interacting Langevin equation. Note that the argument for the Langevin is dimensionless, so either B-fields or H-fields may be used.

$$u(t) = H_1(t)/H_{sat} = B_1(t)/B_{sat} \text{ input field} \quad (3)$$

$$p(t) = M(t)/M_{sat} \text{ output polarization} \quad (4)$$

$$\chi = M_{sat}/H_{sat} \text{ SPIO's } MH \text{ slope} \quad (5)$$

Now transcendental equation can be rewritten in terms of input field, $u(t)$, and output polarization, $p(t)$:

$$p(t) = \mathcal{L}(u(t) + \beta p(t)), \beta \equiv \alpha\chi \quad (6)$$

This single dimensionless parameter, $\beta \equiv \alpha\chi$, is a very powerful predictor of the chain's magnetic behavior. Since $\chi \approx 600$ mT/6 mT=100 and $\alpha$ could range from 0.01 to 0.2 depending on how closely packed SPIOs exist in the chain, values of $\beta$ between 1 and 20 are anticipated.

Positive Feedback, Resolution Improvement, and Schmitt Triggers

Figure 5:
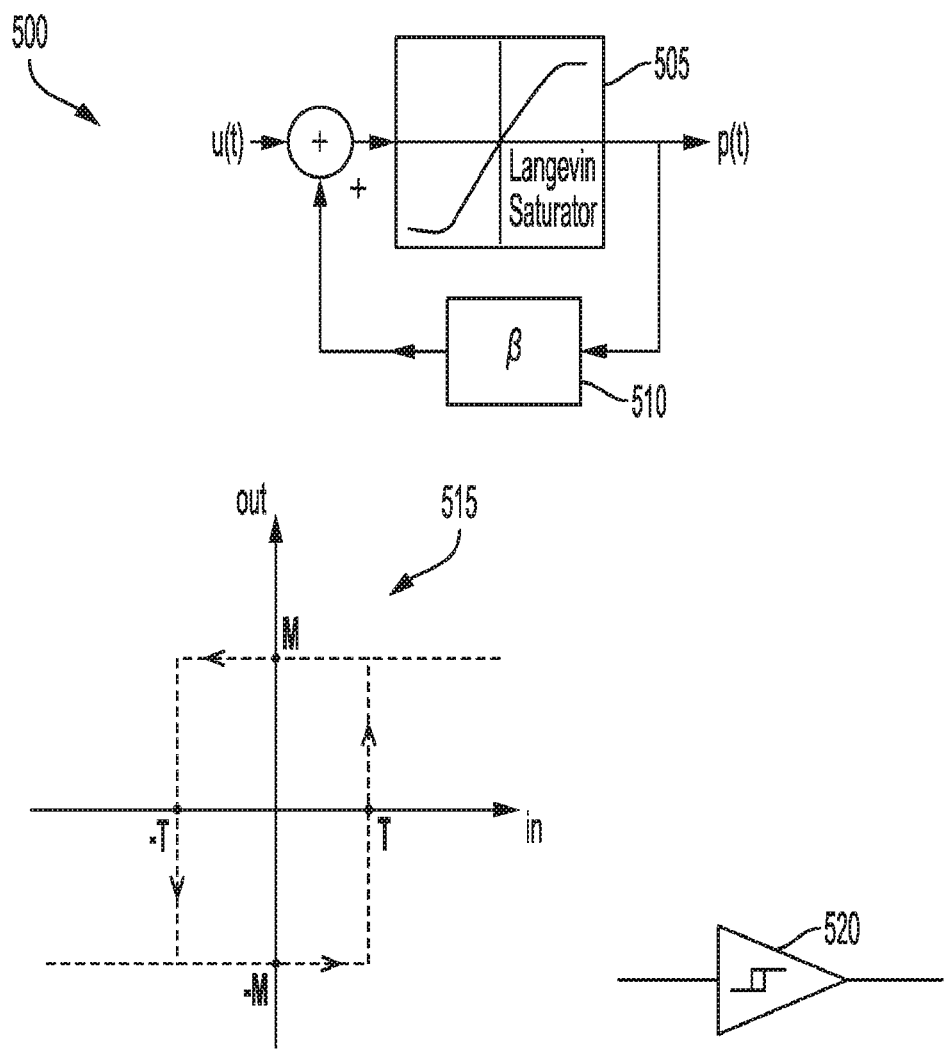
FIG. 5 conceptually illustrates a saturating positive feedback control system, analogous to a Schmitt Trigger comparator circuit.

It is instructive to think of this equation above as a positive feedback control system, with input field, $u(t)$ and output polarization, $p(t)$. See FIG. 5, which conceptually illustrates a saturating positive feedback control system 500, analogous to a Schmitt Trigger comparator circuit, modeled using equation (6) above. For small inputs, $|u(t)| \ll \frac{1}{2}$, the Langevin saturator can be approximated as unity gain, with no saturation.

Figure 14:
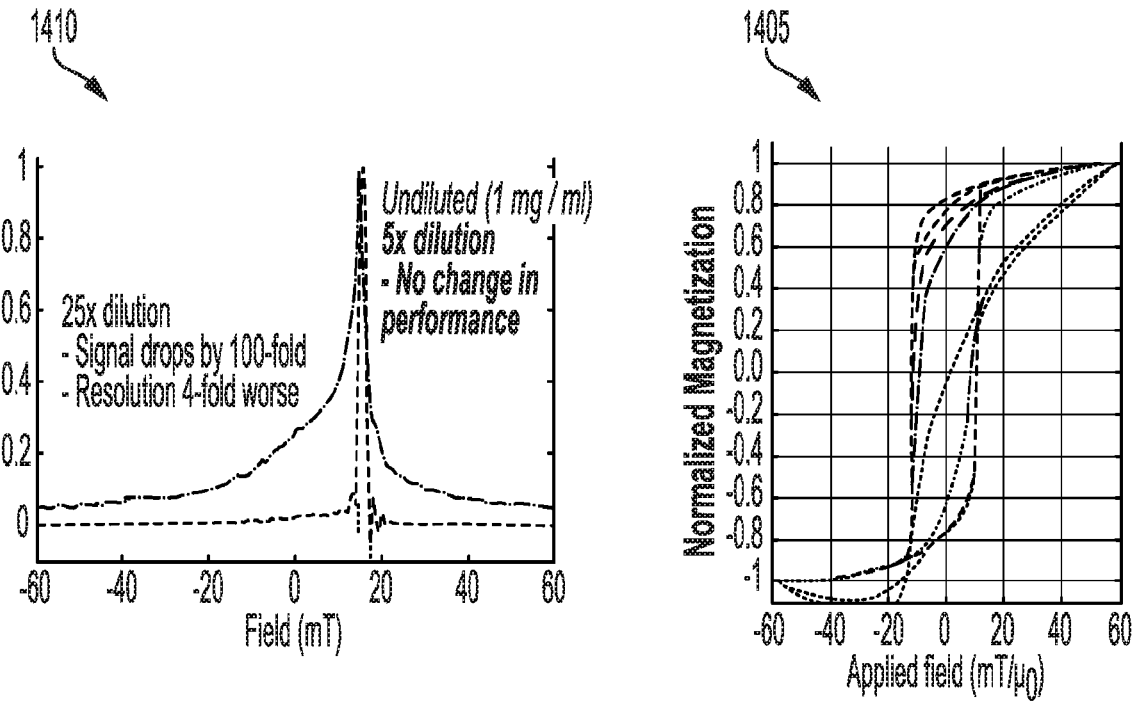
FIG. 14 demonstrates concentration latching in siMPI.

Since the Langevin function 505 saturates and the delay term 510 introduces hysteresis, the output 515 will be very similar to a Schmitt trigger, whose symbol 520 is an op-amp with a hysteresis curve. Essentially, like a Schmitt trigger which is a comparator circuit with hysteresis that occurs via applying positive feedback to the noninverting input of the amplifier, the siMPI multi-particle structure applies positive feedback via local fields to the input field felt by each particle, and the Langevin behavior of each individual particle gives us the saturator component. Experimental data showing hysteresis curves from the nanoparticles that look a lot like Schmitt trigger input-output curves is shown in FIG. 14 described below.

By the normalization definition, $u(t) = \frac{1}{2}$ will induce $p(t) \approx \frac{1}{2}$, and saturation will come gradually as $|u(t)|$ exceeds $\frac{1}{2}$. This means the slope of the (normalized, dimensionless) Langevin saturation is unity, $\partial \mathcal{L}/\partial u = 1$, but this is only valid for weak fields, $|u(t)| \ll \frac{1}{2}$. Under this weak input approximation, the nonlinear control system becomes linear in the input $u(t)$. One can recursively trace through each of the loops (there are an infinite number) through the (linearized) control system to obtain this linear output $$p(t) = u(t)(1 + \beta + \beta^2 + \beta^3 + \ldots) \quad (7)$$

The convergence of this infinite sum hinges entirely on whether $|\beta| > 1$. The sum diverges if $|\beta| > 1$.

$$p(t) = u(t)(1/(1-\beta)) \text{ iff } |\beta| < 1 \quad (8)$$

$$p(t) \to \text{sign}(u(t)) \text{ iff } |\beta| > 1 \quad (9)$$

Interpreting these small-input asymptotic results is a bit troubling at first. The simulation results 600 in FIG. 6 test intuition and "prove" these asymptotic results. Clearly, the simulation backs up some key take-home points:

First, positive feedback always improves spatial resolution, since $|u(t)||1/(1-\beta)| > |u(t)|$ for $|\beta| < 1$.

Second, near-infinite improvement in resolution if $|\beta| > 1$. Note that $\beta = \alpha\chi$ and a larger, higher-resolution resolution SPIO should have cubically stronger $\chi$. The falloff term ($\alpha$) should not change much with radius of SPIO, since dipole fields fall off as $(a/z)^3$. This implies the core SPIOs should still be high resolution to ensure $\beta > 1$. But there appears to be little benefit to pushing from $\beta = 2$ to $\beta = 10$; most likely relaxation would dominate blur for both. This may be great since 40 nm SPIOs may not be needed. Smaller 20 nm (or even 10 nm) might provide regenerative feedback provided they are packed tightly enough.

Third, clearly this adiabatic model, which neglects relaxation, is not fully accurate and that relaxation will dominate experimental resolution.

Fourth, even $\beta=0.1$ is very similar to $\beta=1E-9$, demonstrating how crucial the regenerative feedback condition $\beta>1$ really is.

Fifth, nonlinear, positive feedback with net gain greater than 1 is precisely what makes a Schmitt Trigger latch so effectively. This describes the "chain gain" effectively.

Figure 6:
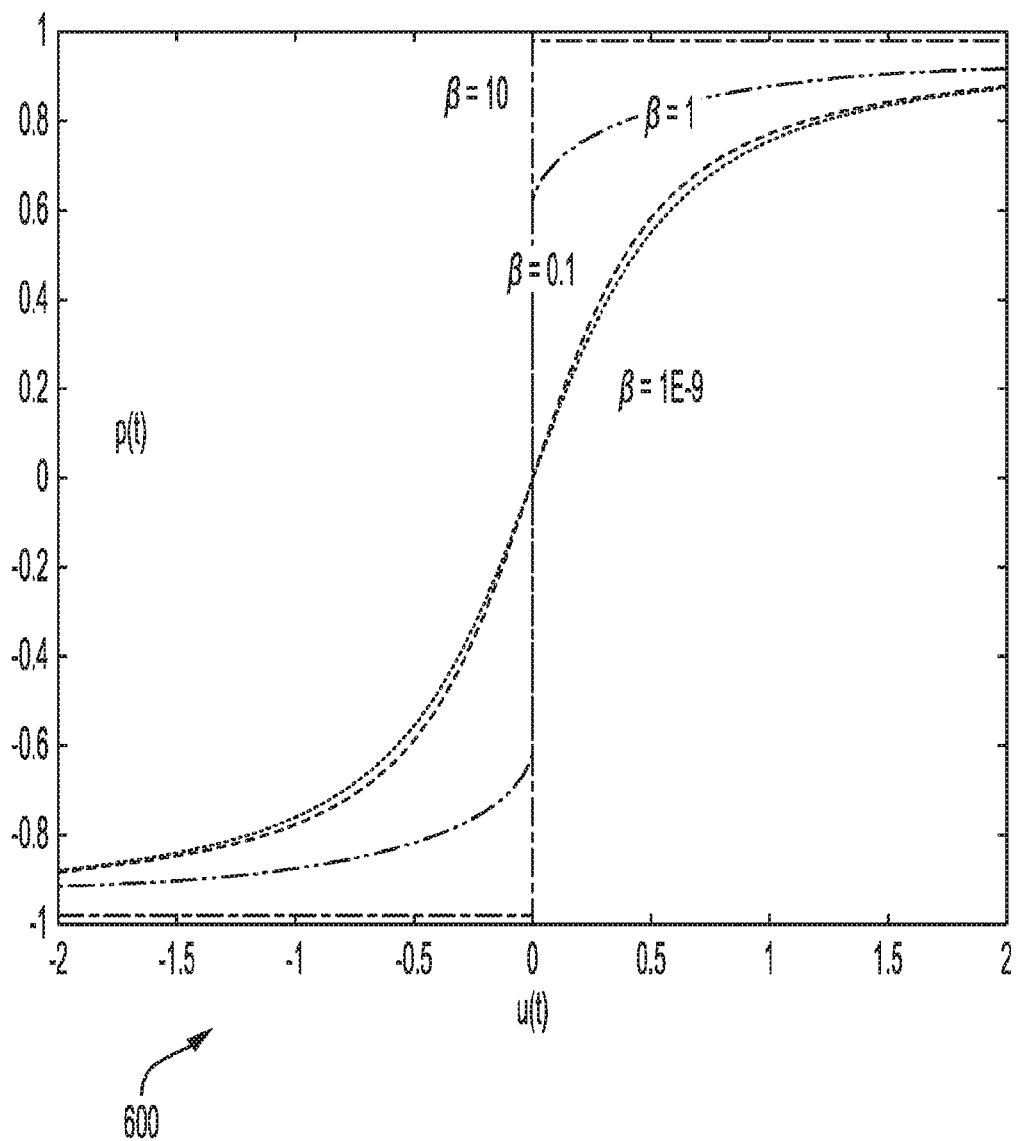
FIG. 6 illustrates Schmitt Trigger behavior with positive feedback.

As illustrated in FIG. 6, Schmitt-trigger behavior is seen for $|\beta|>1$. This indicates that resolution gain with strongly interacting particles is significant. More realistically, relaxation will dominate resolution in this case. The noninteracting case is well modeled by both $\beta=1E-9$ and $\beta=0.1$, which demonstrates the power of positive feedback with $\beta>1$.

A better approximation of the Langevin operator can be found via power series. If $v$ is the input to the Langevin function, $$\mathcal{L}(v) \approx v \partial \mathcal{L}/\partial v \quad (10)$$

Hence, $$p(t)=u(t)\partial \mathcal{L}/\partial u(1+\partial \mathcal{L}/\partial u \beta+(\partial \mathcal{L}/\partial u)^2 \beta^2 + (\partial \mathcal{L}/\partial u)^3 \beta^3 + \dots) \quad (11)$$

The convergence of this infinite sum hinges entirely on whether $\beta|\partial \mathcal{L}/\partial u|>1$. The sum actually diverges if $\beta'=|\beta \partial \mathcal{L}/\partial u|>1$.

$$p(t)=u(t)(1/(1-\beta')) \text{ iff } |\beta'|<1 \quad (12)$$

$$p(t) \to \text{sign}(u(t)) \text{ iff } |\beta'|>1 \quad (13)$$

Positive feedback is the cause of the dreaded "squelch" when a microphone is placed too close to the speakers. If the net audio loop gain from microphone to amplifier to speaker exceeds 1, then positive feedback creates a loud squelch, which means the speakers have hit their saturation limits, just like $p(t)=\pm 1$. If the net gain is less than 1 then the noise is quieter than the voice or music. This is also analogous to positive feedback in a Schmitt trigger comparator. To quote Wikipedia: "In electronics, a Schmitt trigger is a comparator circuit with hysteresis implemented by applying positive feedback to the noninverting input of a comparator or differential amplifier . . . Circuits with hysteresis are based on the fundamental positive feedback idea: any active circuit can be made to behave as a Schmitt trigger by applying a positive feedback so that the loop gain is more than one." See, https://commons.wikimedia.org/w/index.php?curid=528681.

Can Incorporating Relaxation Predict Coercivity?

Coercive behavior is not seen in the above simulations or in the asymptotic analysis for adiabatic chains. However, these simulations are static, and the solutions above are steady-state. So, the coercivity remains a bit of a mystery but, importantly, the high resolution does not depend on the manifestation of coercivity. The Schmitt Trigger does have RC delays, but the literature asserts that hysteresis is seen regardless of delay. One possibility is that a time delay between $u(t)$ and $\alpha(t)$ is essential to manifest hysteresis. When relaxation is incorporated into the model (see FIG. 7, described below):

$$p(t) = 1/\tau e^{-\frac{t}{\tau}} * \mathcal{L}(u(t) + \beta p(t)) \quad (14)$$

This equation shows that coercivity should occur at values of $u(t)=\pm\beta'$. That translates to coercivity at $H_1=\alpha\chi H_{sat}$. Confirmation of this result in simulation and in experiment suggest using scanning waveforms that avoid minor loops and deal with coercivity with safe dB/dt and safe SAR and good SNR and speed.

Figure 7:
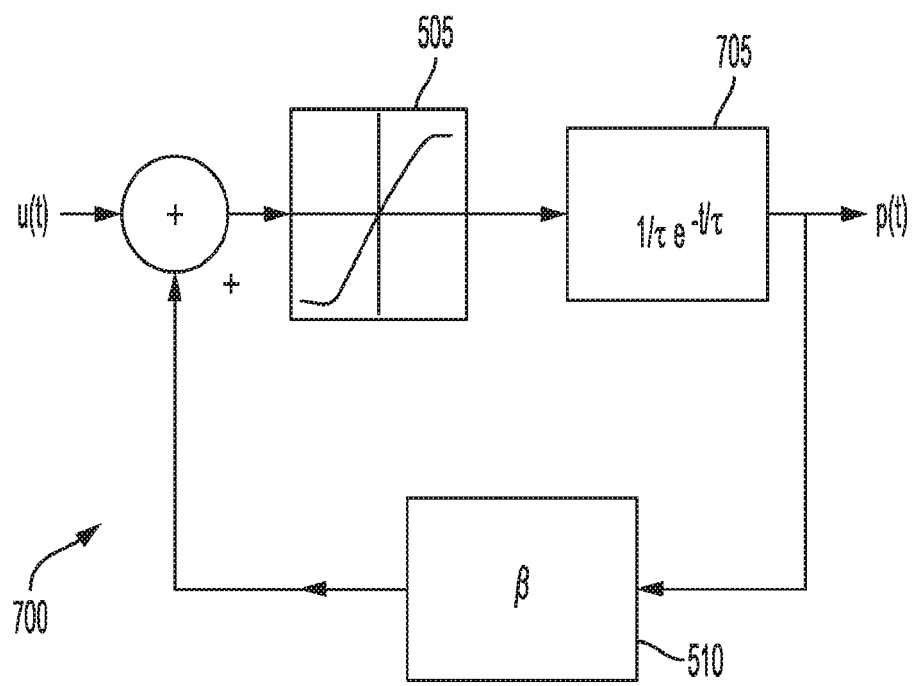
FIG. 7 conceptually illustrates a strongly interacting magnetic nanoparticle model that incorporates a first-order time constant for relaxation.

FIG. 7 illustrates incorporating a first-order time constant 405 for relaxation into the strongly interacting MNP model 700 described above with reference to FIG. 5. It seems unlikely that this (Néel) relaxation time constant, $\tau$, will be the same as the $\tau$ measured for similar SPIOs at noninteracting concentrations; that is, chain formation could easily alter the relaxation time.

Testable Experiments

An imaging theory in possession of a good resolution fortune, must be in want of testable experiments. Some predictions from the above model:

Hysteresis. Coercivity and the fact of prior latching might be explained by the modified interacting Langevin model, where the fast input $u(t)$ gets out of phase with the slowly relaxing chain. This should be testable in simulation, but relaxation cannot be turned off in experiment.

Scaling Rules. It should be possible to estimate Core size a from TEMs, e.g. using simple dipole field equations based on TEMs of SPIOs frozen under a strong field to measure center-to-center distances. $H_{sat}$ and $M_{sat}$ and the $H_c$ coercivity are also directly measurable from the AWR on noninteracting SPIOs (at low concentration). The model above predicts that coercivity should be at $H_1=\chi\alpha H_{sat}$. This should confirm the estimate of $\alpha$ from TEM measurements.

Chain Formation, Viscosity and Concentration. Frozen experiments with and without polarizing fields should be very illuminating. TEMs on frozen samples should reveal chains if they were frozen under a field strong enough. Follow-up AWR measurements with frozen samples should show anisotropic behavior, with Néel relaxation unaffected. A slow, strong pre-polarizing pulse may help to form a chain prior to a fast 20 kHz excitation, especially at lower concentrations or in more viscous solutions. The time it would take to form a chain should depend on both concentration and on viscosity of the fluid. Concentration Latching could be explained here by absence of chain formation below a critical concentration. A higher concentration is necessary in higher viscosity fluids or a longer pre-polarizing pulse.

Magnetomotive Force. If all the above is accurate, then the nanocarrier must be made small enough to avoid the magnetomotive force (scales as radius $a^3$) from dominating the viscous drag (scales as a). One promising design would be a spherical nanocarrier (micelle, exosome, liposome, PRINT particle, etc.) just big enough (e.g., roughly 120-nm inside diameter) to contain a short chain, e.g. five to eleven 20-nm SPIOs. The nanocarrier should be spherical, lest the packaging interfere with chain formation. The outside of the nanocarrier should be fuzzy to increase viscous drag. It may be beneficial to employ smaller SPIOs than in noninteracting MPI, since the SIMPI behavior can create wonderful resolution with smaller SPIOs once they form chains. That said, the term 30 is cubically bigger for bigger radii SPIOs, so it all depends on this nonlinear threshold: to chain or not to chain.

REFERENCES

Wilson, Robert J, et al., J. Magn. Magn. Mater. 321.10, 2009.
B. Gleich and J. Weizenecker, Nature 435, 2005.
B. Zheng et al., Nature Scientific Reports 5, 2015.
B. Zheng et al., Theranostics 2016.
X. Zhou et al., Phys. Med. Biology 62, 2017.

R. Orendorff et al., *Phys. Med. Biology* 62, 2017.
E. Yu et al., *ACS Nano* 11 (12), 2017.
E. Yu et al., *Nano Lett.* 17 (3), 2017.
D. Hensley et al., *Physics in Medicine & Biology* 62 (9), 2017.
Z. W. Tay et al. *ACS nano* 12 (4), 2018.
Z. W. Tay et al., *Theranostics* 8 (13), 2018.
Croft, Laura R. et al., *Medical Physics* 43 (1), 2016.
Dhavalikar, R. et al., *Journal of Physics D: Applied Physics* 49 (30), 2016.
Goodwill, Patrick W. and Steven M. Conolly, *IEEE Transactions on Medical Imaging* 29 (11), 2010.
Goodwill, Patrick W. and Steven M. Conolly, *IEEE Transactions on Medical Imaging* 30 (9), 2011.
Goodwill, Patrick W. et al., *IEEE Transactions on Medical Imaging* 31 (5), 2012.
Goodwill, Patrick W. et al., *The Review of Scientific Instruments* 83 (3), 2012.
Goodwill, Patrick W. et al., *Advanced Materials* 24 (28), 2012.
Konkle, Justin J. et al., *PloS One* 10 (10), 2015.
Lu, Kuan et al., *IEEE Transactions on Medical Imaging* December, 2017.
Rahmer, Jürgen et al., *BMC Medical Imaging* 9 (April), 2009.

Strongly Interacting Magnetic Particle Imaging (SiMPI)

Introduction

Conventionally, Magnetic Particle Imaging likes to think about each nanoparticle as an independent, non-interacting magnetic domain. This allows the ensemble of nanoparticles to be well-modeled by the Langevin model of superparamagnetism. Here, the possibility of having nanoparticles close enough to strongly interact is explored. A new method in Magnetic Particle Imaging is demonstrated to exploit these strong inter-particle interactions to achieve (in theory) the ideal step-like magnetization. This would enable very large resolution improvements in theory due to the delta-like point spread function achieved. In addition, the signal strength is also improved by a few orders of magnitude as the magnetization goes from positive saturation to negative saturation very quickly. In practice, without any deconvolution, 100-micron spatial resolution in 2D imaging and more than 100-fold improved sensitivity is observed compared to the current MPI de facto standard, Resovist. In this work, an outline is presented for a theoretical model for how inter-particle interactions can dramatically improve MPI performance and show experimental data demonstrating achieved MPI performance improvements. Practical challenges remaining as well as potential strategies to tackle them are also discussed.

Figure 8:
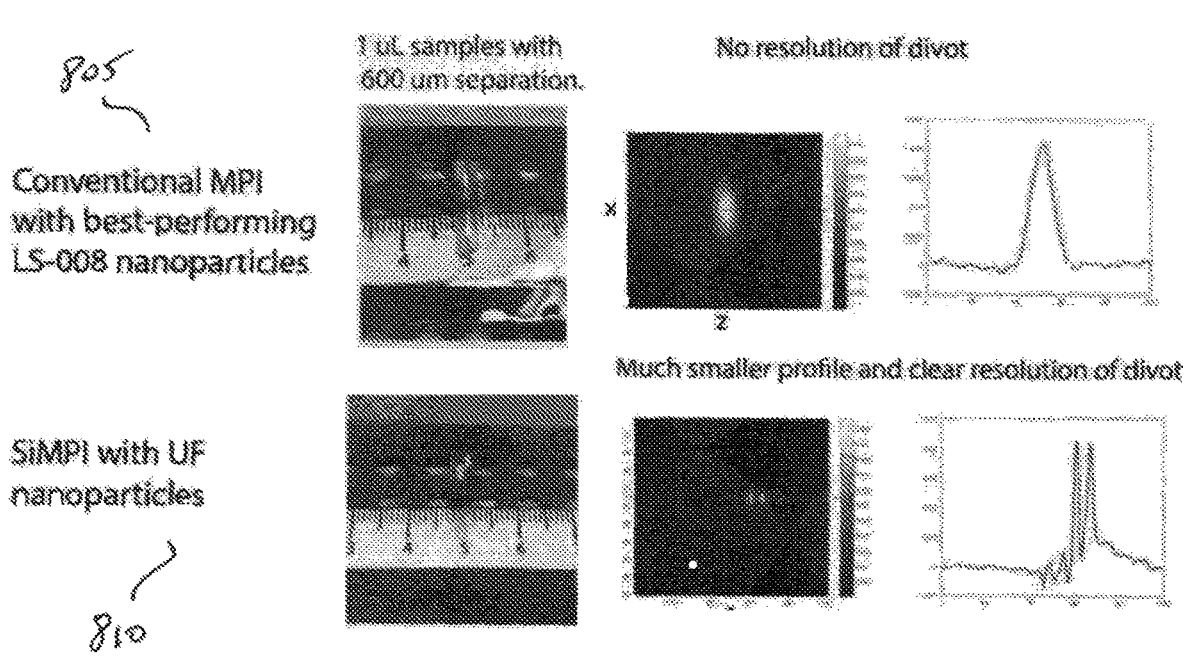
FIG. 8 demonstrates a large improvement using siMPI over best-performing nanoparticles with conventional MPI.

FIG. 8 demonstrates initial results showing the large improvement in resolution with SiMPI over the best-performing nanoparticles with conventional MPI. This is the main motivation of developing SiMPI. For the same phantom of 1 uL samples with 600 um separation, with conventional MPI 805 using best-performing LS-008 nanoparticles, there is no resolution of the divot. With siMPI 810 of the same phantom using UF 30 nm nanoparticles, there is a much smaller profile and clear resolution of the divot.

Theory
Conventional Magnetic Particle Imaging Vs Strongly Interacting Magnetic Particle Imaging In conventional magnetic particle imaging, the nanoparticles are independent single-domain magnetic dipoles that have negligible interactions with each other and are only affected by the external MPI gradient and excitation (drive) fields. As such, models such as the Langevin model look at the ensemble behavior of many individual magnetic dipoles and provide a means to look at the net magnetic behavior from an external observer by summing the (probabilistic) thermal and applied magnetic field effect on each nanoparticle.

This new variant of magnetic particle imaging departs from conventional assumptions and seeks to exploit the effects of inter-particle interactions. Making these interactions very strong reaps the many benefits that will be discussed in more detail below. As a result of this objective, this new way for imaging is referred to as Strongly Interacting Magnetic Particle Imaging (siMPI).

Requirements for SiMPI, Challenges and Initial Solutions

The key aspect of SiMPI is that the nanoparticles are close enough to interact. This requires a few things: (1) The concentration is high enough that nanoparticles have a significant chance to collide in a way that they will "magnetically capture" each other and start forming a nucleus where more and more nanoparticles join, and each of them are close enough to each other to have their magnetic dipoles strongly interact across particles, (2) The outer (non-magnetic) coating or shell of the nanoparticles cannot be too thick such that it prevents close enough proximity between the magnetic cores to strongly interacting, (3) ensuring that all the nanoparticles exist within strongly-interacting multi-particle structures as described above. This is essential since the single, non-interacting, nanoparticle is also able to contribute to the MPI signal but with less desirable imaging characteristics (as will be explained later), and as such, it is the best interest to ensure that all nanoparticles exist within multi-particle structures.

As a result of the three conditions above, some challenges are immediately evident. Firstly, MPI is only a linear and shift-invariant (LSI) system under the assumption that each nanoparticle behaves in the same way and contributes the same way to the MPI signal. Critically, linearity depends on the MPI signal being proportional to the mass of the nanoparticle in the voxel. In point (1) explained above, the nanoparticles can contribute to the MPI signal as individual entities or as part of the multi-particle structure. The ratio of these two states is dependent on the nanoparticle concentration in a non-linear fashion, therefore, in its natural state, SiMPI would be not be LSI due to a concentration latching effect, where SiMPI dominates over a critical concentration and conventional MPI dominates below that threshold. Second, for nanoparticles to be colloidally stable in water, the magnetic core needs to be coated with a hydrophilic coating which is often rather thick. As a result, current SiMPI has only been observed in nanoparticles in organic solvents where there is no hydrophilic coating and magnetic cores are able to approach very close to each other without having a minimum distance set by the hydrophilic coating thickness. Work is currently being conducted to search for a suitable coating that allows phase transfer of nanoparticles to water while maintaining SiMPI properties.

To address these two challenges, an initial solution was developed where the nanoparticles are held within an emulsion of oil droplets inside water. This solves both problems because high local concentrations of nanoparticles are achieved within each emulsion droplet even if the emulsion itself becomes very dilute (for instance, diluted by blood volume after intravenous injection). High local concentrations ensure that essentially all nanoparticles exist within the multi-particle structure when contributing to the MPI signal, solving the concentration latching problem and ensuring maximal benefit since every particle is performing SiMPI rather than being "wasted" as a conventional particle. Also, there is no need for a hydrophilic coating on each magnetic core since the hydrophilic coating is addressed by the surfactant that forms the shell of each emulsion droplet, and therefore, the magnetic nanoparticle cores can almost touch, enhancing the beneficial effects of very strong magnetic interactions between particles. The initial proof-of-concept was performed with a shaken emulsion of 0.2 mg/ml UF RL3 nanoparticles in toluene with DI water. The volume ratio is 1:3, with 1% v/v of Tween-20 or Triton-X as surfactant. Vortexing was done on maximum intensity for 30 seconds, upon which the initial solution forms an emulsion that has the visual appearance of a very light-gray cream/milk.

Figure 9:
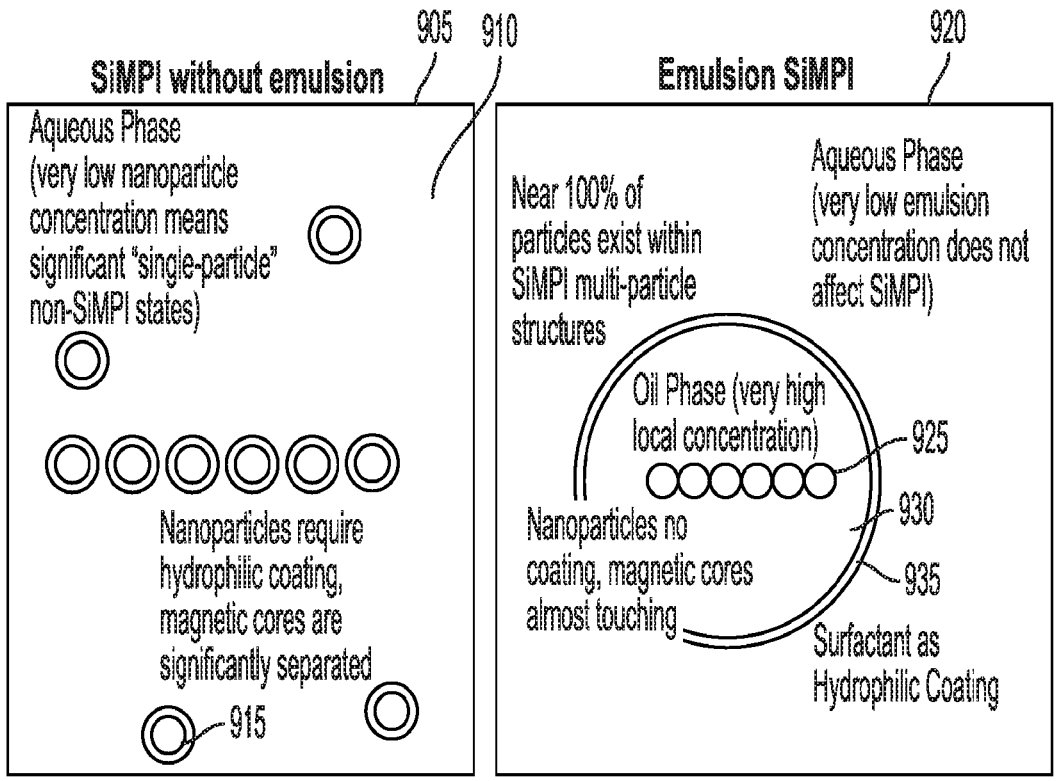
FIG. 9 conceptually illustrates the advantage of an emulsion formulation for siMPI.
Figure 9:
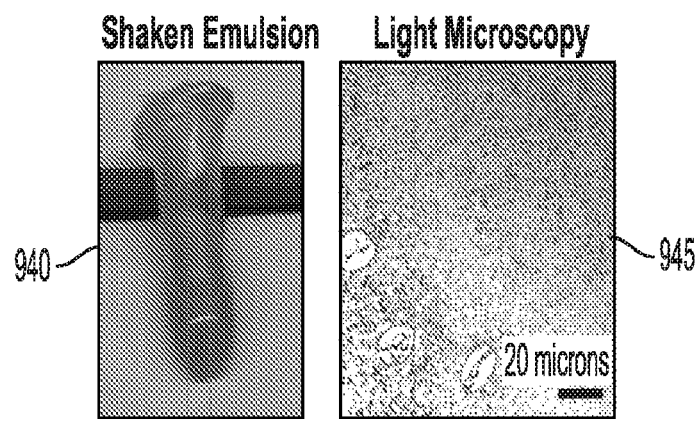

FIG. 9 illustrates the advantage of an emulsion formulation for SiMPI. For siMPI without emulsion 905, the aqueous phase 910 has very low nanoparticle concentration, which means significant "non-siMPI" states. The nanoparticles 915 require hydrophilic coating, so the magnetic cores are significantly separated. For emulsion siMPI 920, the aqueous phase very low concentration does not affect siMPI, since near 100% of the particles exist within siMPI multi-particle structures 925. The oil phase 930 has a very high local concentration, and the nanoparticles have no coating, with magnetic cores almost touching. The surfactant 935 acts as a hydrophilic coating. This is just an initial solution; more robust solutions could potentially have the oil phase replaced by some other (more solid) matrix that sets the nanoparticles in a chain geometry. FIG. 9 also illustrates a photo 940 and light microscopy (100×) 945 of the shaken emulsion. The multi-particle structures are clearly evident (20-micron scale).

Model for Inter-Particle Magnetic Interactions when Particles are in Close Proximity Magnetic Particle Imaging utilizes superparamagnetic iron oxide nanoparticles (SPIONS) that are essentially ferromagnetic single-domain crystal that have a permanent magnetization. However, these behave like a paramagnet when observed as an ensemble due to thermal agitation forces randomizing the directions of the dipole moments of individual crystals. Because each nanoparticle has a permanent dipole moment, they always exert interparticle forces on neighboring particles. In most cases when the suspension is dilute and the particles are far enough apart, these interactions are negligibly weak. The magnitude of the dipole field from a single superparamagnetic iron oxide nanoparticle falls off with distance as follows:

$$B(r) = \frac{\mu_0}{4\pi}\left(\frac{3r(m\cdot r)}{r^5} - \frac{m}{r^3}\right) \quad (15)$$

$$B_{max}(r) = \frac{\mu_0 m}{2\pi r^3}$$

Assuming that the nanoparticles are small enough and sufficiently distant that their shape and size is not important such that both magnets can be modeled as being magnetic dipoles, the interparticle force can be described as:

$$F(m, r) = \frac{-3\mu_0 m^2}{2\pi r^4} \quad (16)$$

where the simplification occurs if r, $m_1$, $m_2$ are all along the same axis. Thus, the interparticle force varies to the fourth-power of the interparticle distance.

For typical SPIOs with core sizes of 15-35 nm and coating thickness of 7-50 nm, (Ferguson, 2015; Tay et al., 2017) interparticle dipole-dipole interactions can be considered negligible for typical in-vivo concentrations. While recent work has shown that for very concentrated SPIO dispersions (>39 mM Fe), magnetic dipole-dipole interactions significantly influence the MPI signal (Them, 2017), most in-vivo concentrations are relatively dilute.

For example, consider a magnetite nanoparticle of 20 nm diameter with a typical magnetic dipole moment m ranging from $10^{-18}$ to $10^{-17}$. For an interparticle distance of 200 nm, the maximum dipole field magnitude at the position of a neighboring particle positioned along the dipole field is approximately 0.25 mT and the maximum inter-particle force is 37.5 fN. This is comparable to typical particle collision forces involved in random thermal Brownian motion that are on the order of 10 fN (Finer, Simmons, and Spudich, 1994). For this case thermal agitation completely randomizes the dipole moment directions and thus, it can be assumed that inter-particle forces are unable to hold particles in a fixed geometry so that particles experience a net local field in one direction from neighboring particles. However, for an inter-particle distance of 20 nm, the dipole field magnitude increases to 250 mT and the inter-particle force is about 37.5 pN. This is orders of magnitude larger than typical Brownian forces that are approximately 0.01 pN and one order of magnitude higher than hydrogen bonds (4 pN) and molecular stepper (kinesin on microtubule) bonds (5 pN) (Finer, Simmons, and Spudich, 1994). Furthermore, this has a positive feedback tendency where the net dipole moment of a chain of two nanoparticles is larger than that of one nanoparticle and is therefore stronger at attracting more nanoparticles to form an even longer chain. As such, it is possible for inter-particle forces to dominate over thermal agitation forces and hold particles in a favorable and stable geometry such as a chain.

Theoretical Conditions Necessary for Local Clustering of Nanoparticles

To evaluate the conditions necessary for local clustering, a simplified 1D analysis is performed of magnetic nanoparticles initially spaced far apart and at random orientations such that the net ensemble magnetization is zero. In this case, the average inter-particle force is zero. Upon application of a homogeneous magnetic field in one direction, the magnetic dipoles align to face the same direction such that the average inter-particle force is at a (angular) maximum. The simple 1D case of particle motion can be modeled by three factors: (1) an attractive magnetic force between particles, (2) viscous drag resisting the motion using Stokes' law for a small sphere, and (3) thermal disordering forces tending to disorder or push apart particles coming together:

$$F_{net}(r) \approx \frac{-3\mu_0 m^2}{2\pi r^4} + 6\pi\eta r_h v + F_{disorder} \quad (17)$$

Given an infinite amount of time to aggregate, the viscous drag term can be neglected and thus the "capture radius" can be calculated as:

$$\frac{3\mu_0 m^2}{2\pi r^4} > F_{disorder} \quad (18)$$

-continued $$r < \left(\frac{3\mu_0 m^2}{2\pi F_{disorder}}\right)^{1/4}$$

For a typical magnetite nanoparticle of 20 nm with typical magnetic dipole moment m of $10^{-17}$ to $10^{-18}$ and assuming $F_{disorder}$=0.01 pN, the capture radius is between 88 nm and 278 nm. This means that the critical concentration (v/v) is between 0.64 to 0.03%. In mg/ml for magnetite, this is about 1.5 mg/ml. Experimentally, this concentration is much higher than the critical concentration of 0.04 mg/ml where the transition occurs between SIMPI behavior and conventional SPIO behavior. Modifying the approximate 0.01 pN value in literature to 0.001 pN and 0.1 fN gives a capture concentration of 0.25 mg/ml and 0.05 mg/ml. A value of 0.1 fN makes sense because the force of a single Brownian collision is 0.01 pN, therefore, the averaged net disordering force from many collisions from different directions will be much lower especially when evaluated only in the direction of the attraction axis.

Another indirect modeling method to calculate this averaged $F_{disorder}$ will be to calculate the diffusion time of a nanoparticle in a viscous media. The time will allow the calculation of diffusion velocity and therefore the viscous drag force. This should approximately be equal to the $F_{disorder}$ value.

Close Proximity and Stable Relative Geometry of Particles Generates Large Local Fields Requiring a Coercive External Field to Overcome Because the magnetically associated particle ensembles have a stable relative geometry, any one particle in the ensemble will feel a large local field caused by its neighbors that are locked in a specific relative geometry to itself. The most stable geometry is that of a chain, where the magnetic dipoles of each particle lines up with the others along a common axis. The relative energy of the applied external field can be evaluated versus the internal local field, referencing prior work from Kornig et al. (2014). The energy from the external applied field can be determined as follows:

$$E_{ext} = -\Sigma_{i=1}^n m_i \cdot B_{ext}$$

$$E_{ext} \approx -nmB_{ext} \cos(\Omega - \alpha) \quad (19)$$

The above assumes that all crystals in the chain have the same angle α to the chain axis and have approximately the same magnetic moment m. Ω is the angle of applied field to the chain axis.

Now consider the energy from the local field generated by dipole-dipole interactions that are referred to as $E_{loc}$ assuming that the neighboring particles have the same angle (ai=aj=a) to the chain axis as the central particle as laid out in (Kornig et al., 2014):

$$E_{loc} = \frac{\mu_0}{4\pi}\sum_{i=2}^n \sum_{j=1}^{i-1}\left(\frac{3(m_i r_{ij})(m_j r_{ij})}{r_{ij}^5} - \frac{m_i \cdot m_j}{r_{ij}^3}\right) \quad (20)$$

$$E_{loc} = -\frac{\mu_0}{4\pi}\sum_{i=2}^n \sum_{j=1}^{i-1}\frac{m_i \cdot m_j}{r_{ij}^3}(3\cos\alpha_i \cos\alpha_j - \cos(\alpha_i - \alpha_j))$$

$$E_{loc} \approx -\frac{2(n-1)\mu_0 m^2}{4\pi r^3}(3\cos^2\alpha - 1)$$

$$E_{loc} \approx -\frac{2(n-1)\mu_0 m^2}{4\pi c^3}(3\cos^2\alpha - 1)$$

where the approximation occurs because only the interactions between neighboring particles are significant and interactions between particles spaced farther apart can be considered negligible. The quantity c is the center-to-center distance between adjacent particles. The local $B_{loc}$ along the chain axis in the 1D case where û is a unit vector along the chain axis, can thus be expressed as follows:

$$E_{loc} \approx (n-1)m \cdot B_{loc} \quad (21)$$

$$B_{loc} = \frac{\mu_0}{4\pi}\sum_{i=2}^n \sum_{j=1}^{i-1}\left(\frac{3(m_i r_{ij})(\hat{u}_j r_{ij})}{r_{ij}^5} - \frac{m_i \cdot \hat{u}_j}{r_{ij}^3}\right) \quad (22)$$

$$B_{loc} \approx -\frac{2(n-1)\mu_0 m}{4\pi r^3}(2\cos\alpha)$$

The H-field that is observed locally by any nanoparticle in the chain can be written as:

$$H_{loc} = H_{ext} + \frac{B_{loc}}{\mu_0} \quad (23)$$

As calculated in the previous subsection, $B_{loc}$ can be as high as 200 mT. Since $B_{loc}$ is much higher than $B_{ext}$ and is aligned with the chain axis, the magnetic moment of the particles remains aligned with the chain axis. This basically acts like a coercive offset in $H_{loc}$. Because $B_{loc}$ is a function of a which in turn is a function of the stability of the chain and the magnitude and direction of the 3D applied field vector H (less and less stable as it approaches the coercive threshold), $B_{loc}$ decreases as $H_{ext}$ approaches the coercive threshold, therefore instantaneously decreasing the coercive threshold. This triggers a positive feedback cascade where $H_{loc}$ is rapidly diminished and the particles align rapidly to $H_{ext}$, effectively causing a large change in $H_{loc}$ locally although there is only a small change in $H_{ext}$. This amplification of the rate of change of $H_{loc}$ is modulated by the time constant of the change in nanoparticle angle α.

The average angle α is related to the ensemble magnetization assuming single-domain particles with constant magnetic moment, m, as follows:

$$M_{loc}(t) = Nm \cos \alpha(t) \quad (24)$$

The local magnetization is also described by the Langevin function but modulated by a time constant to account for the finite delays in the change of the ensemble magnetization. Equation (24) can be substituted in to form a complete equation:

$$M_{loc}(t) = Nm \cdot e^{-t/\tau} * \mathcal{L}(kH_{loc}) \quad (25)$$

$$M_{loc}(t) = Nm \cdot e^{-t/\tau} * \mathcal{L}\left(k\left(H_{ext} + \frac{2(n-1)m}{4\pi r^3}(2\cos\alpha(t))\right)\right)$$

$$M_{loc}(t) = Nm \cdot e^{-t/\tau} * \mathcal{L}\left(k\left(H_{ext} + \frac{2(n-1)m}{4\pi r^3}(2M_{loc}/Nm)\right)\right)$$

$$M_{loc}(t) = Nm \cdot e^{-t/\tau} * \mathcal{L}\left(k\left(H_{ext} + \frac{(n-1)M_{loc}}{N\pi r^3}\right)\right)$$

$$M_{loc}(t) = Nm \cdot e^{-t/\tau} * \mathcal{L}\left(k\left(H_{ext} + \frac{F}{N}M_{loc}\right)\right)$$

where F/N is the ratio of the constant describing the field fall-off to the number density.

Prior work with magnetosome chains has shown that the coercive field is much larger in the geometry of linear chains as opposed to clusters of nanoparticles (Kornig et al., 2014)

where the coercive threshold is lower than 10 mT. This suggests that chains are responsible for the effect observed here since the observed coercive threshold is higher than 10 mT.

Implications and Re-Modeling as a Positive Feedback System—Schmitt Trigger

The previous subsection showed that from an energetics perspective, SPIO chains can be stable and can provide stronger local magnetic fields than possible with the external applied field alone. The local inter-particle fields are strong and provide a form of "remanent magnetization" that opposes changing of each particle's magnetization.

In this subsection, this phenomenon is remodeled as a positive feedback system and draws upon the Schmidt trigger analogy to provide a reference model. First, the field felt by each nanoparticle is rewritten as the sum of the external applied field and the "neighbor" field.

$$H_{net}(t) = H_{external}(t) + \alpha M_{neighbor}(t) \quad (26)$$

Here, the dimensionless alpha term modulates the effect of the SPIOs close-by and depends mostly on the inter-particle distance. Since the magnetic fields of the SPIO (modeled as a single-domain dipole) fall off as $r^3$, the dominant fields are the two adjacent neighbors in the chain. As discussed above, for a small inter-particle distance of 20 nm, the felt-neighbor-field is approximately 250 mT which is an order of magnitude higher than typical MPI excitation amplitudes. However, this falls off quickly with distance and at 200 nm, the field is only 0.25 mT. Clearly, if SPIOs are almost touching each other, the neighbor-field cannot be neglected and strongly-interacting MPI behavior will manifest.

Substituting this into the magnetization equation:

$$M(t) = Nm \cdot e^{-t/\tau} * \mathcal{L}(k(H + \alpha M_{neighbor}(t))) \quad (27)$$

where N|particles m$^{-3}$| is the local number density of magnetic particles at the scale of the interacting chain/crystal, $\alpha$ is a dimensionless coefficient that depends on inter-particle distance and core size, and $M_{loc}(t)$ is the local magnetization at the scale of interacting chain/crystals. Finite relaxation dynamics are also included by convolution of the energy-only relationships with a Debye relaxation kernel, et/z.

To further simplify the equation, it can be rewritten with normalized dimensionless terms, simply concerned with the (dimensionless) polarization of the SPIO (normalized to the maximum (saturated) ensemble magnetization $Nm = M_{sat}$. The applied field is made dimensionless by normalizing to $H_{sat}$, which is the applied field needed to achieve $M_{sat}$. The following definitions are used:

$$u(t) = H(t)/H_{sat} \quad (28)$$

$$p(t) = M(t)/M_{sat} \quad (29)$$

$$\beta = \alpha M_{sat}/H_{sat} = \alpha \chi_{SPIO} \quad (30)$$

The magnetization equation thus becomes:

$$M(t) = Nm \cdot e^{-t/\tau} * \mathcal{L}\left(H + \alpha M_{loc}(t) \frac{1}{H_{sat}}\right) \quad (31)$$

$$p(t) = e^{-t/\tau} * \mathcal{L}(k(u(t)) + \beta p(t)) \quad (32)$$

where k is a constant to adjust the input argument of the Langevin to achieve Langevin saturation.

This is clearly a positive feedback system and as $\beta$ increases, the positive feedback becomes stronger and results in a smaller applied field required to cause ensemble saturation of magnetization. MPI SNR improves linearly with $M_{sat}/H_{sat}$ and spatial resolution improves approximately linearly with smaller $H_{sat}$. Thus, using positive feedback to force ensemble magnetization to saturation allows $H_{sat}$ to become smaller with linear improvements to both SNR and spatial resolution. With good values for $\beta$, in theory, $H_{sat}$ approaches zero and therefore both SNR and spatial resolution can be improved near infinitely. This can be understood from the fact that the ideal MPI magnetization response of the SPIO is a step function with step at H=0 since dM/dH which is the MPI point-spread-function would be an (near) infinitely tall delta function which gives infinitely good SNR and spatial resolution. However, this feedback circuit has a "delay term" as magnetization does not occur instantaneously. Therefore, for realistic scanning times, the ensemble magnetization may not be able fully polarize and therefore infinitely good MPI performance will not be achieved. Continuous rastering of the FFP also imply that there will be some blurring of signal between voxels since by the time positive feedback finishes polarizing the SPIOs in a voxel, the FFP may have moved through several voxels, thus "smearing" signal between voxels and causing some inevitable blurring (rather than delta-function-like perfect spatial resolution). Nevertheless, this method of exploiting positive feedback is a very powerful method to improve MPI performance and should still give dramatic improvements in MPI performance.

To analytically solve this positive feedback equation, the Langevin operator must be approximated as $\mathcal{L}(x) \approx x \partial \mathcal{L}/\partial x$ and that the relaxation time constant is small enough such that near-infinite feedback loops can occur within the scan time. The equation can thus be approximated as a power series:

$$p(t) \approx u(t) \partial \mathcal{L}/\partial x (1 + \partial \mathcal{L}/\partial x \beta + (\partial \mathcal{L}/\partial x)^2 \beta^2 + (\partial \mathcal{L}/\partial x)^3 \beta^3 + \ldots) \quad (33)$$

If $|(\partial \mathcal{L}/\partial x)\beta| < 1$, this infinite series converges (since $1/(1-x) = 1 + x + x^2 + \ldots$) to:

$$p(t) \approx u(t) \cdot \frac{\partial \mathcal{L}/\partial x}{1 - (\partial \mathcal{L}/\partial x)\beta} \quad (34)$$

If $|\beta| > 1$, this infinite series simply "hits the rails":

$$p(t) \approx \text{sign}(u(t)) \quad (35)$$

Again, note the potential of strongly-interacting SPIOs to vastly improve MPI performance, since when $\beta > 1$, the output of the system is simply sign(u(t)) which means that the SPIO magnetization response is a perfect step function. This translates to, in theory, infinitely good SNR and spatial resolution.

Figure 10:
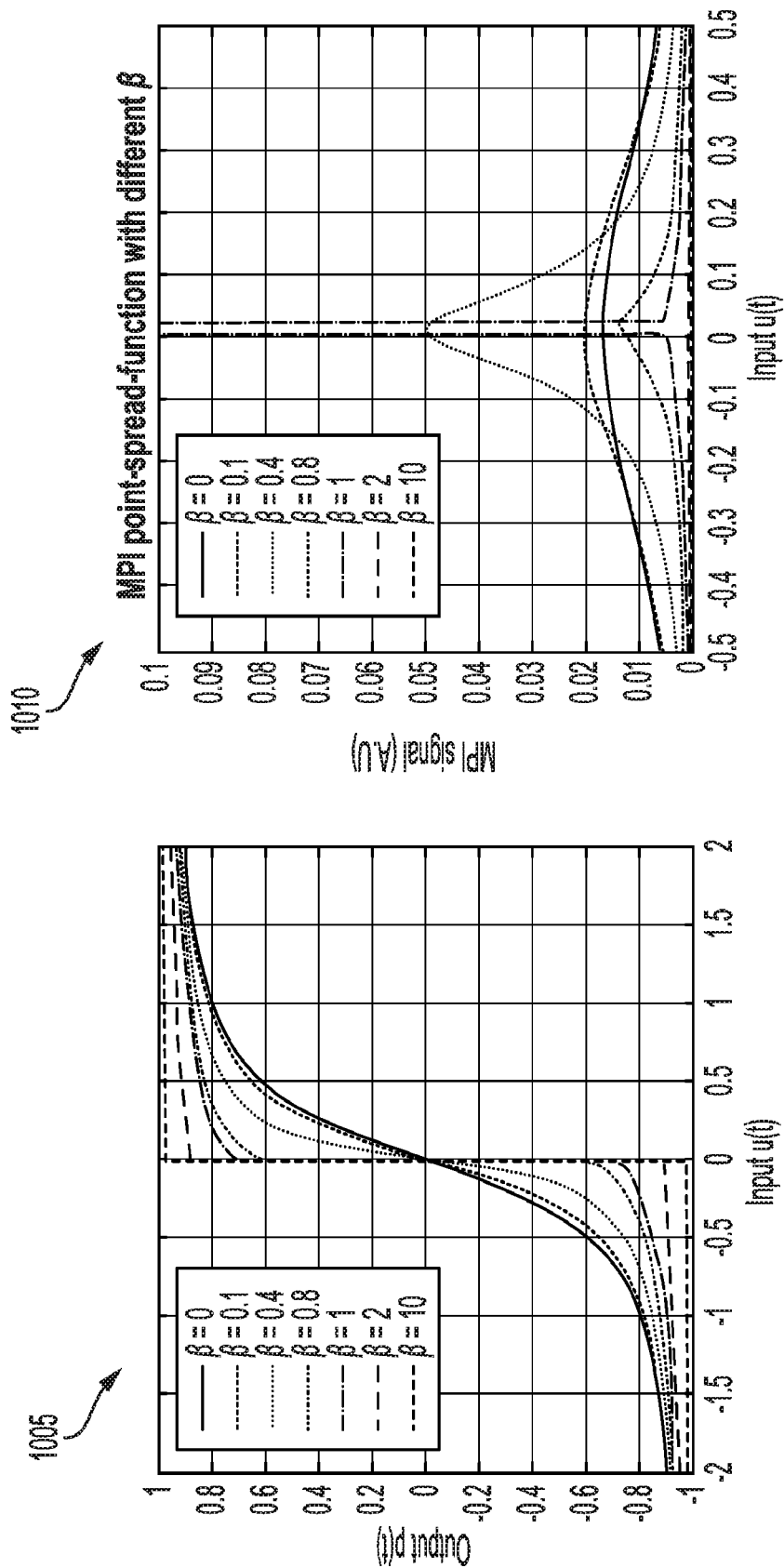
FIG. 10 demonstrates simulated plots of the input and output of the siMPI positive feedback system without considering relaxation delays.

The theoretical input-output of the SiMPI positive feedback system is plotted in FIG. 10 for various values of $\beta$. These simulations 1005 plot the input u(t) and output p(t) of the SiMPI positive feed-back system without considering relaxation delays (the Debye relaxation term is ignored). 100 recursions of the positive feedback loops were used in the simulation. As $\beta$ approaches and goes above unity, the siMPI system becomes more and more like a step function, which promises near infinitely good SNR and spatial resolution for MPI in theory, as evident from the corresponding point-spread function plot 1010. In practice however, relaxation delays limit the number of recursions through the feedback loop and therefore limit the output of the positive feedback since scanning times must be realistic and cannot afford to "wait" forever for near-infinite feedback loops to occur.

Analysis Involving SPIO Relaxation

From the previous subsection, one important caveat is that the relaxation term must be accounted for, as the positive feedback has a delay term. This will set an effective limit and therefore the M-H curve will not be a perfect step function. This also implies that there will be some (dynamic) hysteresis as for a continually changing applied H field, by the time the delay is factored in, the applied field would have moved significantly from the zero crossing and thus the delayed positive feedback magnetization change will not be located at the zero point (or the sign-change point). The stronger the relaxation term, the greater the width of the hysteresis as shown in the simulated plots from FIG. 11, described below. This is the theoretical basis for the minimum threshold drive amplitude for siMPI, and explains why at lower excitation frequencies, the minimum threshold drive amplitude further decreases. In theory, at very low excitation frequencies, there should be no hysteresis and no excitation amplitude threshold. In practice however, a minimum threshold is still observed, as seen in FIG. 12, discussed below. This is likely the result of the stability of the chain, since the Langevin equation depends on thermal-magnetic equilibrium to describe the change in ensemble magnetization. Because the chain is exceptionally stable once formed, at zero applied field, it may take a much longer time than predicted by the Langevin model for the chain to "fall apart" and have the net magnetization randomize to zero. As such, there is a necessary minimum coercive energy input threshold to force the SPIO chain to reverse magnetization polarity and give siMPI signal.

Figure 11:
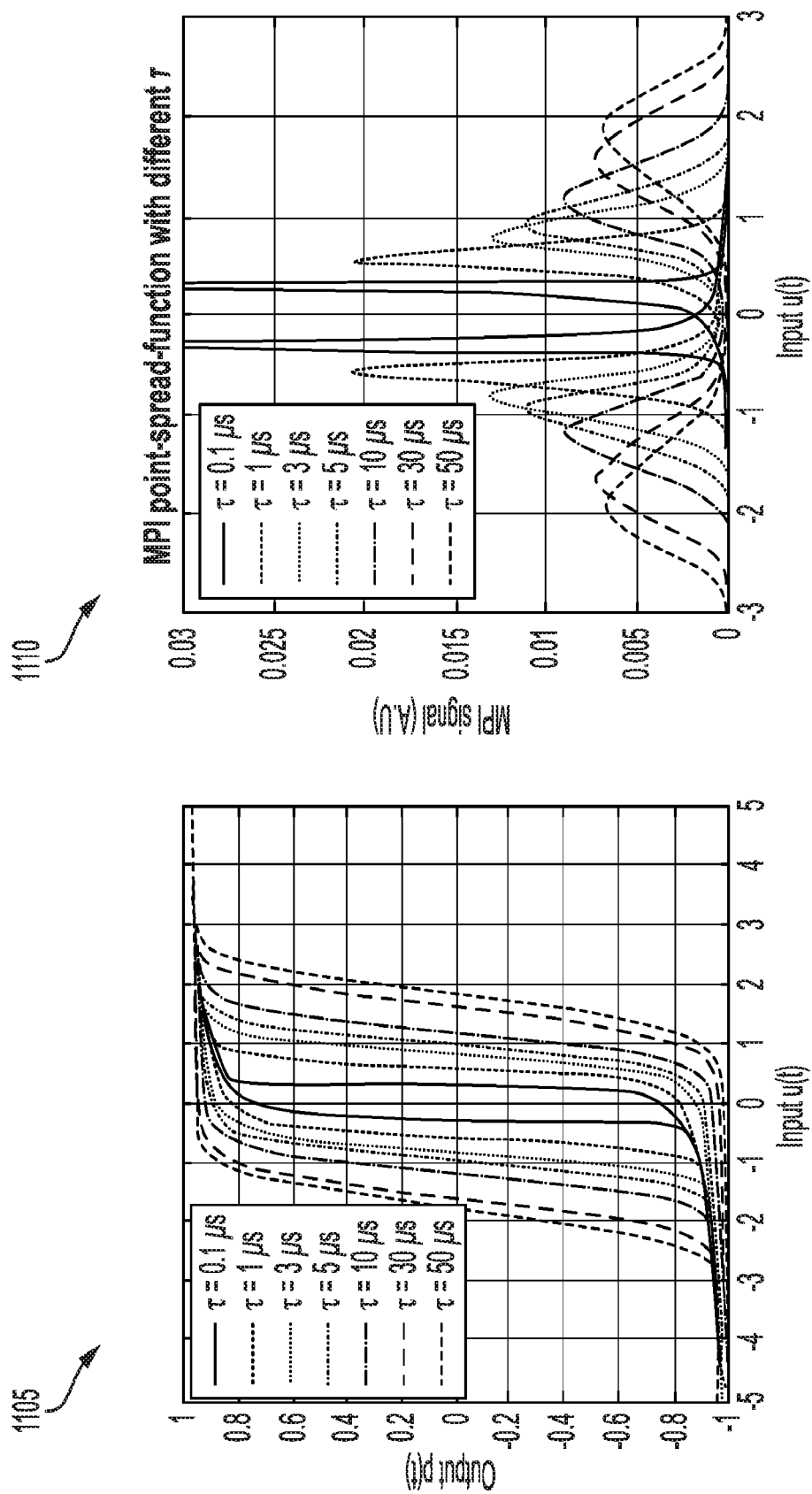
FIG. 11 demonstrates simulated plots of the input and output of the siMPI positive feedback system, taking relaxation delays into account.
Figure 12:
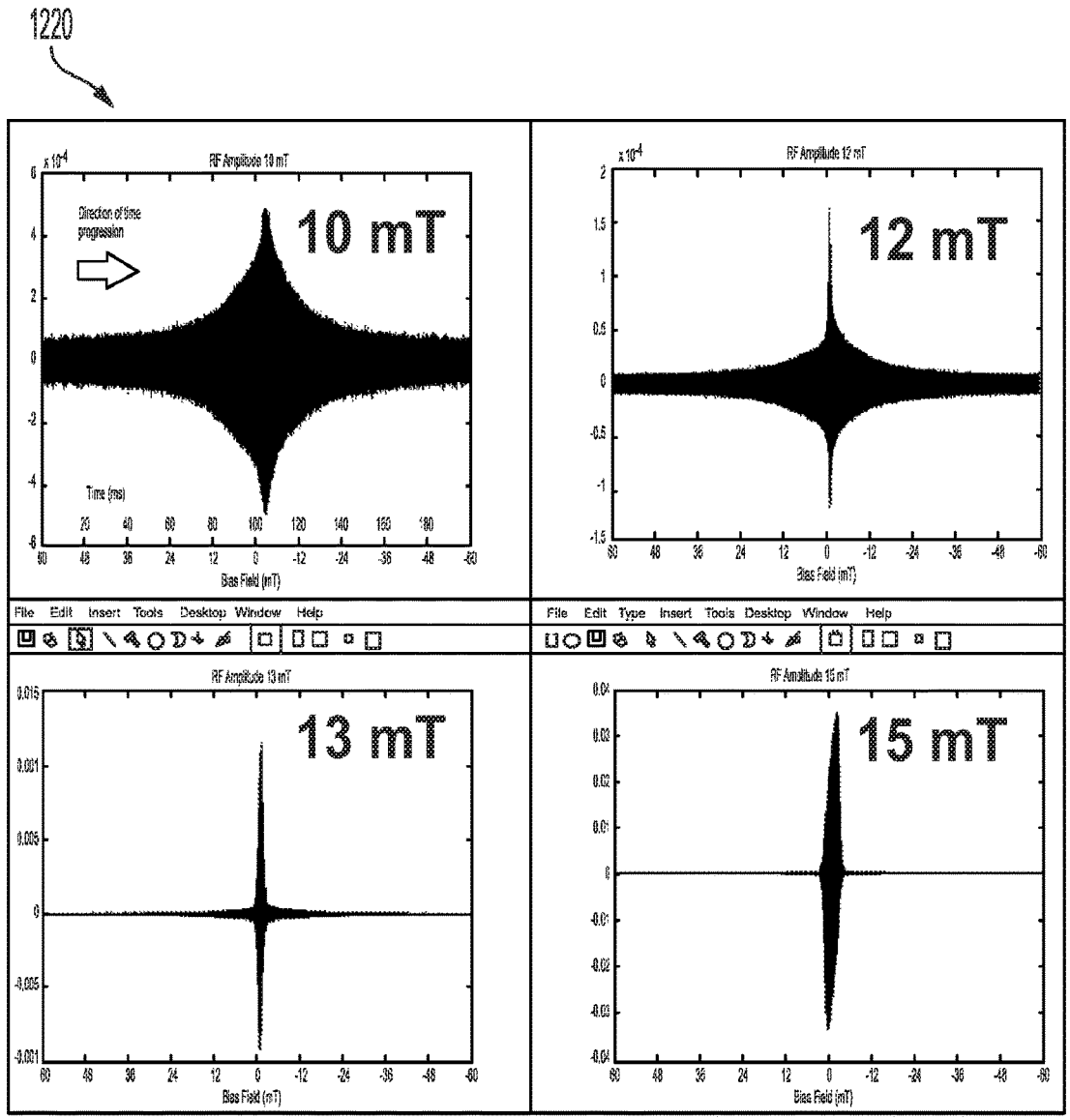
FIG. 12 demonstrates the effect of drive/excitation amplitude on siMPI.

FIG. 11 illustrates plots of the input u(t) and output p(t) 1105 (and corresponding PSF 1110) of the siMPI positive feedback system taking relaxation into account. In this scenario, hysteretic behavior is observed which is similar in appearance to experimentally obtained data and point-spread-function. Simulation parameters use a linear u(t) slew from −5 to 5 over a duration of 25 µs which is a half-period of the typical 20 kHz MPI excitation. The reverse slew is then performed to complete the slew in the other direction and finish off a full period, forming complete hysteretic loops. β=1 was assumed and strong field dependence of the time constant was assumed: $\tau(u(t))=\tau_{base}\exp(-10u(t)/u_{max})$ if u(t) is opposite sign of p(t), otherwise $\tau(u(t))=\tau_{base}$. Various (Debye) relaxation time constant $\tau_{base}$ was used, showing the dependence of the hysteresis width on relaxation time constant. The shorter the relaxation time constant, the better the siMPI performance.

Another factor to take note is that the time constant for relaxation has a strong applied field dependence (Deissler, Wu, and Martens, 2014). For example, the Neel time constant changes by more than 3 orders of magnitude going from zero applied field to 20 mT. The Brownian time constant changes by more than 10-fold as well for the same range of applied fields. As such, it may also be the case that positive feedback loops are occurring at very low drive amplitudes, but because the time constant for relaxation is so long, the rate of change of magnetization from one polarity to the other polarity (even if β>1) takes a very long time. Since the MPI signal is proportional to dM/dt, this results in very low signal strength and siMPI-like peaks are hard to observe. On the other hand, if the drive amplitude is higher, even if the frequency is very low, the time constant decreases significantly as the drive amplitude increases from zero to the peak amplitude. As a result, the magnetization change occurs most rapidly close to the peak of the drive waveform, and since MPI signal is proportional to dM/dt, this rapid magnetization change is observed as an offset (hysteretic) peak characteristic of the sharp signal peaks expected of siMPI. Therefore, the "minimum" drive amplitude may be caused in part by the reduction in relaxation time constant with applied field.

Parameters Governing SiMPI

As seen from the previous subsection, the value of β and thus α are key to siMPI performance. These parameters are dominated by the inter-particle spacing. This subsection provides an in-depth definition of these important parameters.

The dimensionless interaction factor β can be calculated as follows, using the geometry of the dipolar field and assuming the ideal linear chain:

$$a = 2k\left(\frac{r}{c}\right)^3 \tag{36}$$

where c[m] is the center-to-center distance between adjacent particles and r[m] is the core radius. The assumption is that the effect of the two neighboring particles are dominant and particles further away exert negligible effect due to the r/c term since c=2c. Further, k<1 is a lossy factor to account for the fact that magnetization at the surface of the single-domain nanoparticle is less than the particle magnetization.

This leads to β being:

$$\beta = 2k\left(\frac{r}{c}\right)^3 \frac{M_{sat}}{H_{sat}} \tag{37}$$

and since $M_{sat}$ is usually about 0.6 T/µ0 for bulk magnetite and $H_{sat}$ is usually about 6 mT, this results in the approximate equation:

$$\beta \approx 200k\left(\frac{r}{c}\right)^3 \tag{37}$$

As long as the distance between particles is not too big, β>1 which leads to saturating positive feedback (the magnetization "hits the rails" as soon as the sign changes from positive to negative).

Recommended Modifications to X-Space Scanning

Because the time delay may not be trivial, in order to implement SiMPI robustly, it is recommended that either the excitation frequency is lowered significantly from the standard 20 kHz in order to allow time for positive feedback loops to saturate the magnetization, or that the excitation amplitude is maintained to be high such that it counteracts the saturating term to allow the net input to change sign. However, this results in "dynamic hysteresis" and requires changes to the x-space reconstruction since the point spread function will now be offset from the zero applied field point. The former recommendation is better in that there will be no offset from the zero point, but the very low frequency will result in much lower SNR since MPI's signal is proportional to the rate of change of magnetization.

Recommended Modifications to X-Space Reconstruction

To reconstruct the MPI image properly when a hysteretic point spread function is observed, all data must be thrown out and only data after the coercive threshold should be used. This prevents the MPI gridding algorithm from averaging zero signal with the SiMPI signal and resulting in non-linearity due to the two states of the nanoparticle. Next, since the point-spread-function is offset, this needs to be accounted for since the position of the point source is offset in the image. To address this, it is recommended to take the average of the two positions in the positive and negative slew direction images, since the offset will be in different directions. Basically, a cross-correlation algorithm can calculate the offset between the two images, and the final image can simply be one of the images with axis offset by a half of the calculated offset from the algorithm.

Experimental Results

Drive Amplitude Needs to be Higher than Coercive Threshold

FIG. 12 illustrates the effect of drive/excitation amplitude on SiMPI. If drive amplitude 1205 is below the threshold, SiMPI behavior is lost and the conventional MPI response is seen, which is a few orders of magnitude weaker in SNR 1210 and almost an order of magnitude poorer in resolution 1215. To show that SiMPI is not merely a reconstruction artifact or trick, raw time-domain data 1220 from the MPI receiver coil is shown as drive amplitude is changed. As time passes, the background near-DC field is very slowly ramped down and passes zero. The zero point of the background field corresponds to center of the time course. Broad envelopes are observed and then a very sharp peak as the drive amplitude reaches the threshold, showing the switch from conventional MPI to SiMPI behavior. The strength of the raw signal changes by orders of magnitude as well. The slight broadening of the envelope in 15 mT plot is due to the envelope widening since there is more leeway above the coercive threshold of 14 mT and thus MPI signal is seen when the background field is at zero and when it is near zero (<1 mT away as well, hence, the broadening of the envelope. Critically, this suggests that with a drive amplitude equal to the siMPI amplitude threshold, an image can be directly formed from the raw time domain envelope, opening opportunities to reduce reconstruction computational load and time as well as possibility of demodulation of the AM signal (the envelope) and thus using a much lower receive bandwidth.

As illustrated in FIG. 12, the drive amplitude needs to be higher than a threshold to generate siMPI behavior. This ties in with the model where the input argument to the Langevin saturator must be made to change sign by a "coercive" external input term to cancel the remanent magnetization term from neighboring particles. This is a dynamic "coercive" threshold, because of the relaxation/delay term, the siMPI system cannot instantly respond to changes in applied field, and thus there is a large remanent field from neighboring particles. If a long time is given for the siMPI system to respond to changes in the externally applied field, very little or no coercive offsets/threshold are expected.

Lower Drive Frequencies Decrease the Coercive Threshold

Figure 13:
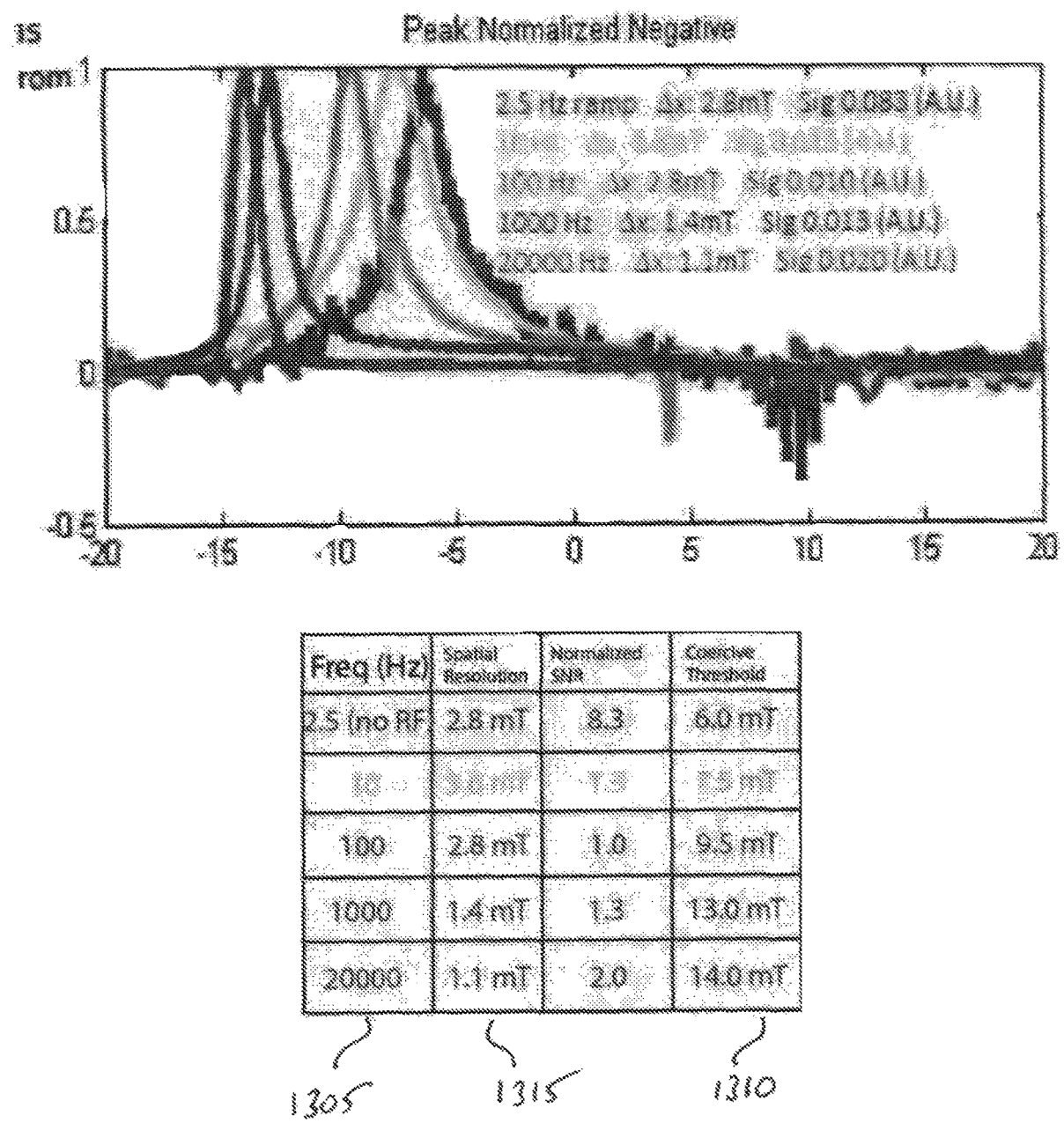
FIG. 13 demonstrates the effect of drive/excitation frequency on siMPI.

In FIG. 13, the effect of frequency on SiMPI is investigated. Lower frequencies 1305 lower the coercive threshold 1310, and this is likely due to there being more time to deal with the delay in the positive feedback loop, therefore less applied field is needed for the input argument to switch sign and saturate in the other direction (thus generating the step response and the sharp dM/dt peak received in MPI). However, the spatial resolution 1315 also worsens, possibly because there is more time spent near zero field where thermal forces are able to break apart the chain structure, therefore resulting in a mix of siMPI and non-siMPI behavior.

Requirement of a Minimum Particle Concentration

FIG. 14 illustrates concentration latching in siMPI. Below a certain threshold concentration, the dynamic hysteresis curves 1405 no longer show "step-like" behavior and the point spread functions 1410 become broader. siMPI behavior is lost and MPI performance degrades to conventional levels. Note the dynamic hysteresis curves at high concentrations look very similar to the input-output function of a Schmitt trigger.

The data in FIG. 14 shows that a minimum concentration is required for robust siMPI behavior, below which, the point-spread-function worsens significantly and SNR drops. This can be understood as the point-spread-function being a weighted combination of two SPIO states: where one state is the high SNR, high resolution but offset peak siMPI state and the other state is the centered, low SNR, low resolution conventional MPI peak. The fact that the worsening of the point-spread-function always "blurs" more towards the center than the edges suggests that the blurring is simply the conventional (centered peak) MPI state becoming more and more dominant in the mixed siMPI and conventional MPI signal. To ensure LSI properties, it is thus critical to operate above this threshold concentration to avoid having a combination of two states (siMPI and non-siMPI) of the nanoparticle and being unable to linearly quantify nanoparticle mass.

Also, experiments in solid-at-room-temperature dodecane solvent show that coercive effect is suppressed, suggested that close proximity is required for the observed effect.

2D Imaging

Figure 15:
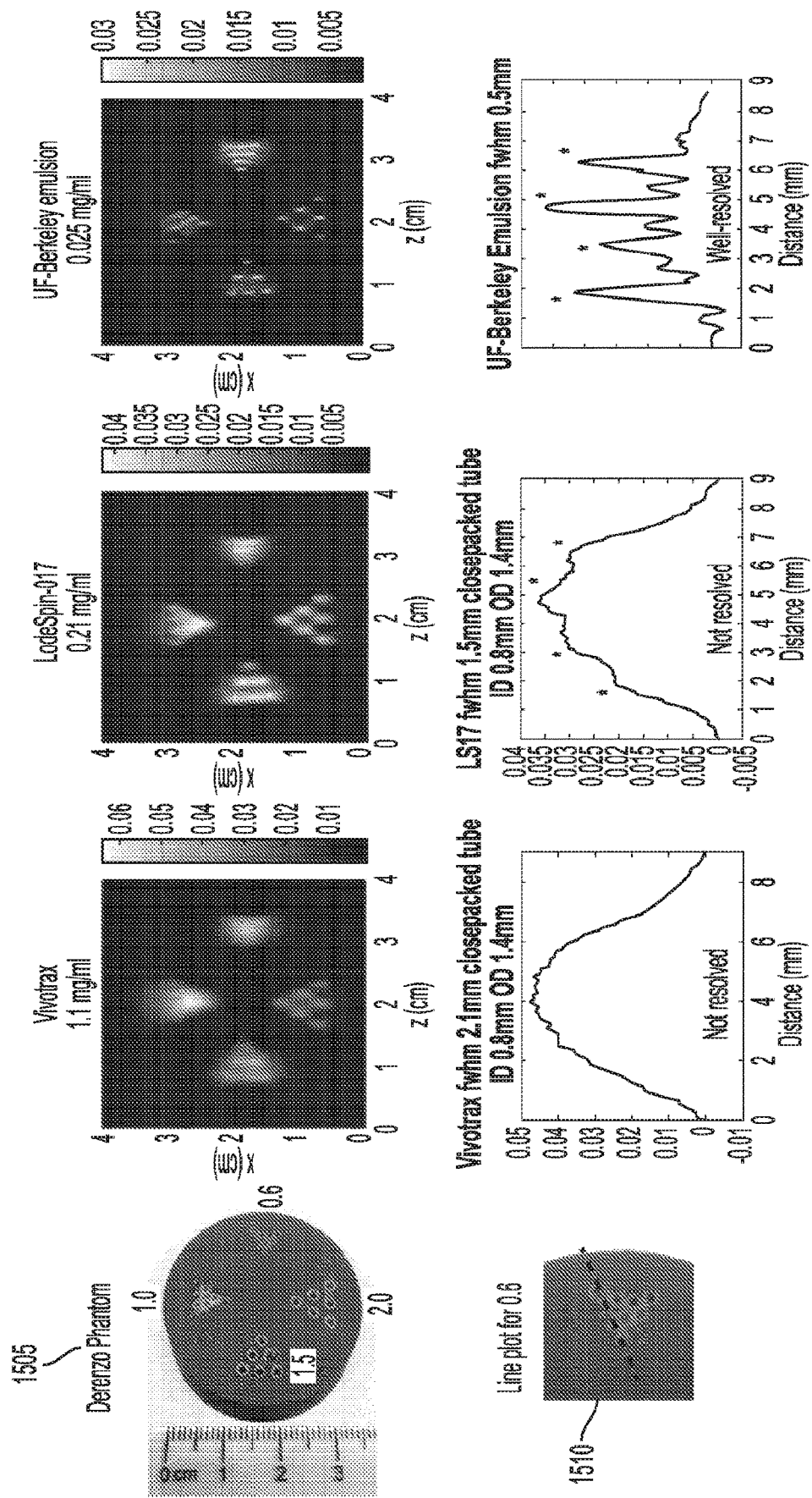
FIG. 15 illustrates an improvement in imaging performance with siMPI using various 2D phantoms.
Figure 15:
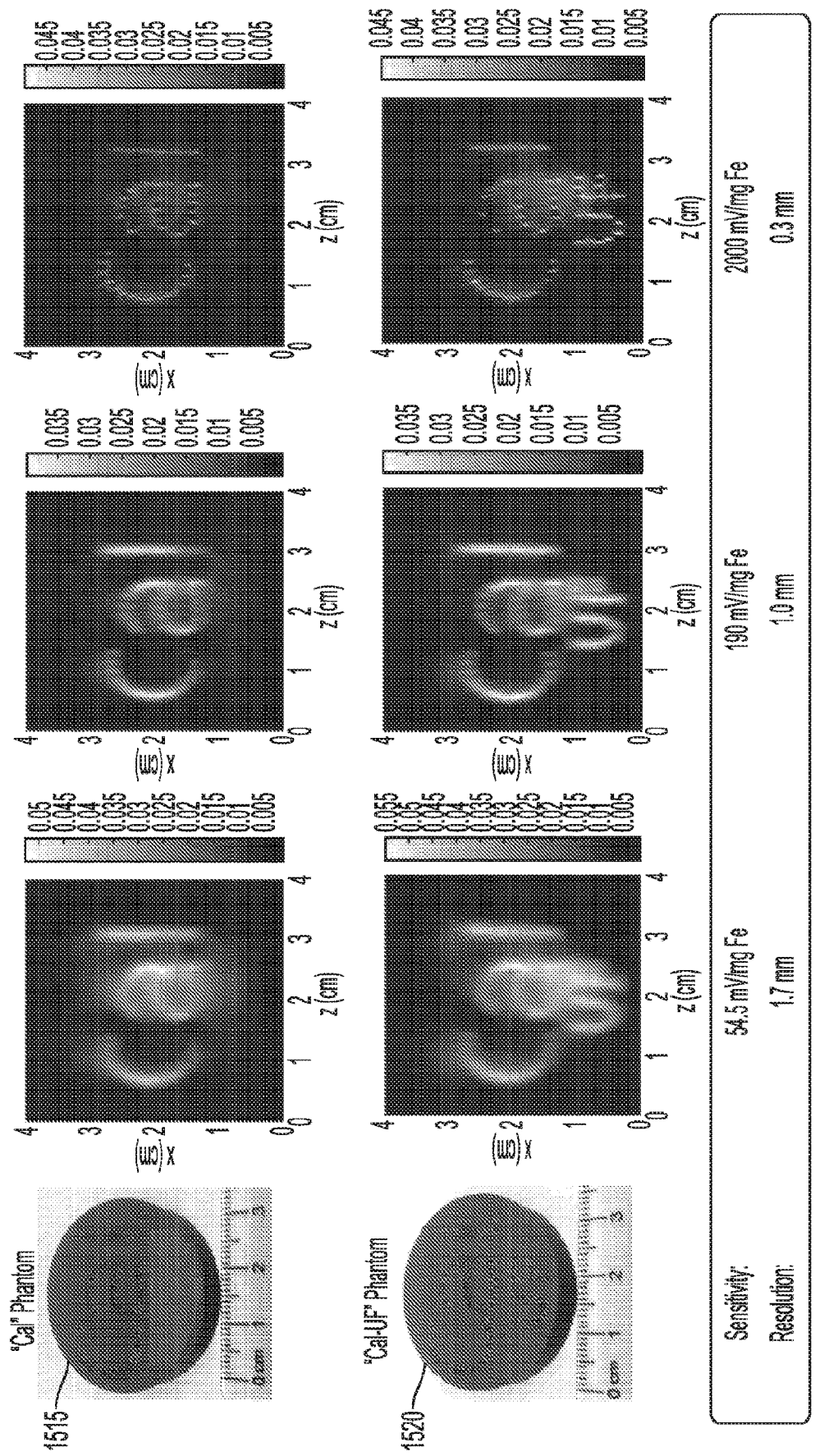

FIG. 15 demonstrates 2D imaging results that clearly show large improvements in spatial resolution and SNR with siMPI. Clear images are still obtained even though concentrations were almost 2 orders of magnitude lower than standard MPI tracers and conventional MPI scanning. Images are acquired on a Derenzo phantom 1505, a line plot 1510, the "Cal" phantom 1515 and the "Cal-UF" phantom 1520.

TEM Images Prove Chain Formation

Figure 16:
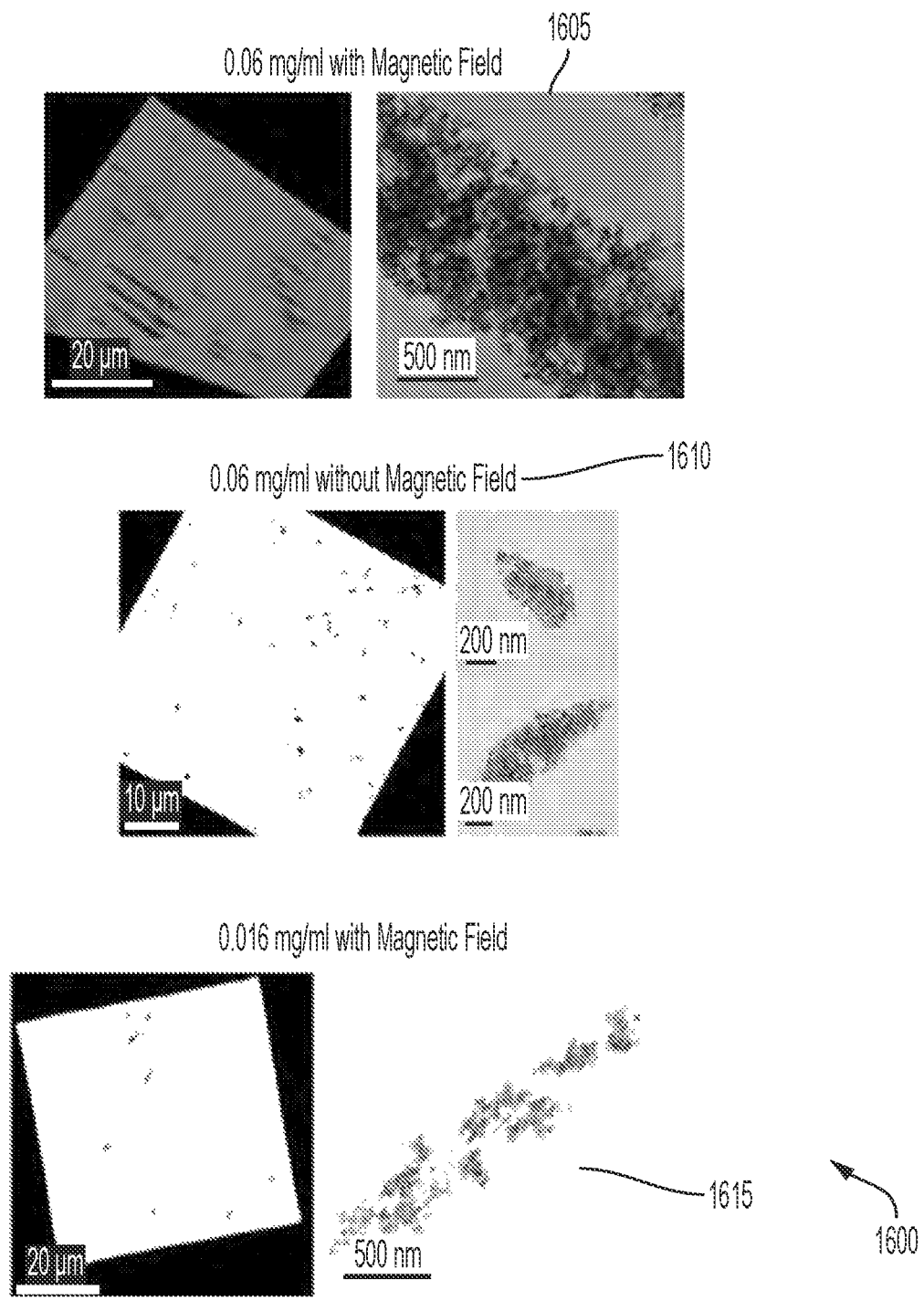
FIG. 16 demonstrates TEM imaging that shows clear formation of particle chains when a magnetic field is applied.

To verify the model's premise that magnetic chains of nanoparticles are formed, TEM images of the RL3 nanoparticles were taken at different polarizing fields. The results are shown in FIG. 16. TEM imaging show clear chain formation when a magnetic field is applied. At low concentrations, chains barely form due to abovementioned concentration latching effects.

Figure 17:
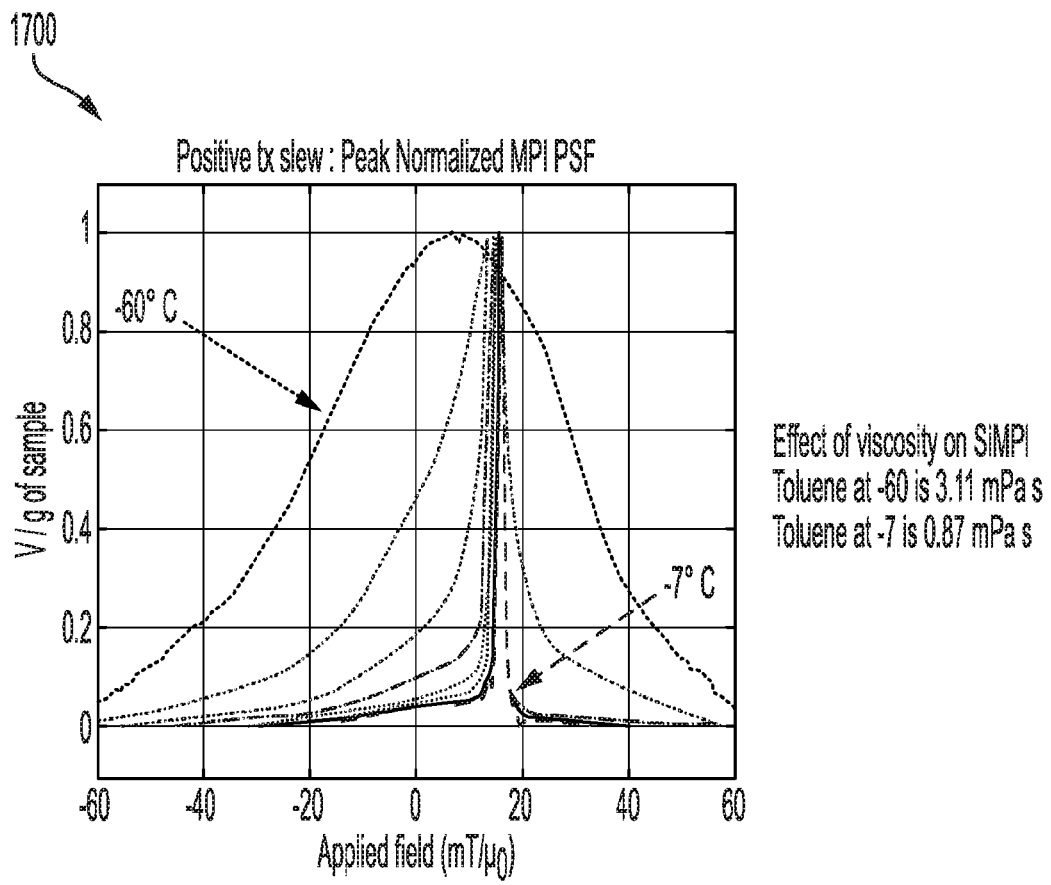
FIG. 17 demonstrates how temperature is used to change the toluene viscosity to affect the siMPI nanoparticles.

Prepolarizing Pulse can Help Ensure SiMPI Behavior by Giving Time for Chain Formation First, viscosity does affect SiMPI behavior because the more viscous the media, the longer the time is required for chain formation to enable SiMPI. See FIG. 17, which illustrates that temperature was used to change the toluene viscosity to affect the SiMPI nanoparticles. Higher viscosity shows poorer SiMPI performance as the nanoparticles have greater difficulty coming together to form chains needed for SiMPI.

Figure 18:
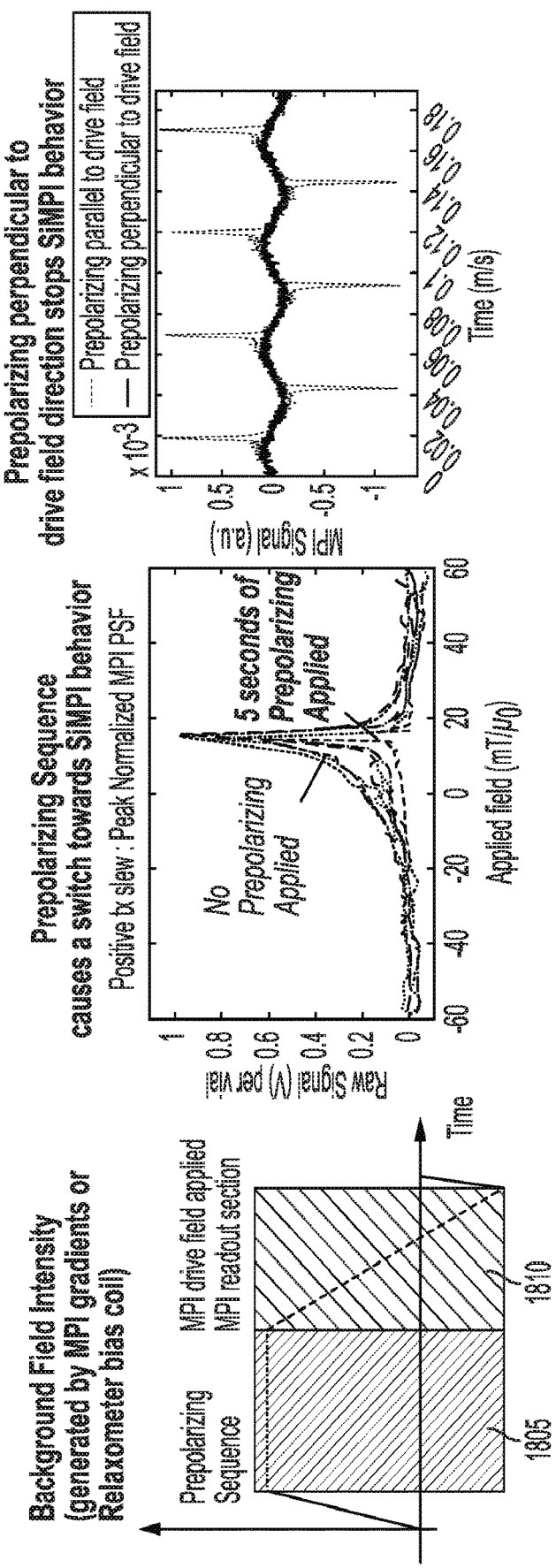
FIG. 18 conceptually illustrates (left) a pre-polarizing pulse to form the siMPI chain prior to performing the siMPI scanning and readout, demonstrates (middle) how the pre-polarizing pulse generates siMPI behavior where there was no siMPI prior due to the lack of a pre-existing chain, and demonstrates (right) how the pre-polarizing pulse must be parallel to the drive field direction.

To address this, a pre-polarizing pulse can be used to form the SiMPI chain before performing the MPI scanning and readout. The results of this strategy are shown in FIG. 18, which is described below. This allows SiMPI to be robust to concentration latching effects by using a pre-polarizing pulse to ensure almost all nanoparticles exist within SiMPI structures/chains.

In FIG. 18, a pre-polarizing pulse 1805 is used to form the SiMPI chain before performing the MPI scanning and readout 1810. The pre-polarizing pulse generates siMPI behavior where there was no siMPI before due to lack of a pre-existing chain. The pre-polarizing pulse must be parallel to the drive field direction to work. The perpendicular case suppresses SiMPI behavior completely.

SiMPI Behavior Requires Nanoparticle Chain to have its Axis Parallel to RF Excitation Axis When the nanoparticle chain has its axis perpendicular to the drive field excitation axis, SiMPI does not occur at all. This makes sense because the initially formed long chain of particles is unable to quickly re-orient to match the drive field excitation axis. Furthermore, from the geometry, the neighboring particles now actually provide a de-magnetizing field when they get polarized in the (perpendicular) direction by the drive field, and rather than positive feedback, negative feedback is observed and very poor MPI signal/performance is observed.

This is good for SiMPI images however, since the typical EPI raster trajectory used means that in conventional MPI the field-free-point passing just above or below the nanoparticle generates blurring MPI signal by inducing some rotation of the nanoparticle magnetic moment to point in the other direction from the field-free-point. This is known as the tangential envelope in prior MPI work Lu et al., 2017 and creates a wispy haze that reduces perspicuity and effective resolution of the MPI images. If instead of conventional MPI, SiMPI is used, the fact that parallel background and drive axes is required mean that there will only be SiMPI when the field-free-point rasters through the nanoparticle, and there will be no SiMPI signal when the field-free-point passes just above or below (effectively the background field direction is perpendicular to the drive axis). This acts as natural suppression of the tangential envelope, and therefore non-hazy MPI images can be obtained even without multi-channel acquisition as required in Lu et al., 2017.

CONCLUSION

The results shown here show the great promise of SiMPI to very significantly improve MPI spatial resolution and SNR. However, much work remains to be done to robustify the chemical formulation in order to maintain SiMPI behavior under all circumstances (in vivo, at different polarizing fields etc.). Especially with regards to a safe (the toluene used in this initial work is not considered to be a desirable compound to be injected), colloidally stable formulation, this chemistry work into a nanocarrier or appropriate "shell" for SiMPI multi-particle structures will be vital to enable in vivo scans with SiMPI.

REFERENCES

Ferguson R M, Khandhar A P, Kemp S J, Arami H, Saritas E U, Croft L R, Konkle J, Goodwill P W, Halkola A, Rahmer J, Borgert J, Conolly S M, Krishnan K M. Magnetic particle imaging with tailored iron oxide nanoparticle tracers. IEEE Trans Med Imaging [Internet]. 2015 May; 34(5):1077-1084. Available from: http://dx.doi.org/10.1109/TMI.2014.2375065 PMCID: PMC4428902

Tay, Zhi Wei et al. (2017). "The Relaxation Wall: Experimental Limits to Improving MPI Spatial Resolution by Increasing Nanoparticle Core size". In: Biomed Phys Eng Express 3.3.

Them, K. On magnetic dipole-dipole interactions of nanoparticles in Magnetic Particle Imaging. Phys Med Biol [Internet]. 2017 May 3; Available from: http://dx.doi.org/10.1088/1361-6560/aa70ca PMID: 28467324

Finer, J T, R M Simmons, and J A Spudich (1994). "Single myosin molecule mechanics: piconewton forces and nanometre steps". In: Nature 368.6467, pp. 113-119.

Kornig, Andre et al. (2014). "Probing the mechanical properties of magnetosome chains in living magnetotactic bacteria". In: Nano Lett. 14.8, pp. 4653-4659.

Deissler, Robert J, Yong Wu, and Michael A Martens (2014). "Dependence of Brownian and N'eel relaxation times on magnetic field strength". In: Med. Phys. 41.1, p. 012301.

Lu, K et al. (2017). "Multi-channel Acquisition for Isotropic Resolution in Magnetic Particle Imaging". In: IEEE Trans. Med. Imaging PP. 99, pp. 1-1.

Embodiments

Some embodiments of the invention include a Magnetic Particle Imaging (MPI) system that includes a field-free line (FFL) within the magnetic field having an axis and a center or a field free point (FFP); a VLF range drive field homogeneous magnetic field that effectively rasters the instantaneous FFP or FFL over the 3D field of view (FOV); magnetic nanoparticles disbursed throughout an animal or human, with biomechanical, vascular or biochemical targeting to reveal normal anatomy or pathophysiology; a slow shift field to move the partial field of view pFOV across the body; at least one VLF (20 kHz to 3 MHz typical bandwidth) to receive the induction signal from the magnetic nanoparticle; filters to reject direct feedthrough signal (typically at the first or low harmonics of the drive frequency) and a low-noise preamp to amplify the signals; an antialiasing filter and analog to digital converter (ADC) to digitize the induction signal after the preamp and the digitized signal is stored on a computer for image reconstruction; and a reconstruction algorithm to create an image of magnetic nanoparticle distribution with linearity and shift invariance (x-space reconstruction method or system matrix).

In some embodiments of the invention, the fast slew field-free-region trajectory amplitude exceeds the coercivity threshold of a high concentration assembly of superparamagnetic nanoparticles, which behaves like a ferromagnetic heterostructure. Compelling data has been acquired (see above) showing that the very strong induction signals and very high spatial resolution and MPI signals can be obtained when the drive field exceeds the coercive threshold.

In some such embodiments, the image reconstruction algorithm corrects for the positional shift in the MPI signal due to coercivity, which alternates sign in accordance with the phase of the drive field. Several algorithms can correct for this artefactual, alternating sign image displacement. In x-space reconstruction, the simplest method is to shift the reconstructed location on positive phases of the drive field by B_coercivity/G; and for negative scans, the location is shifted by −B_coercivity/G. This can also be corrected within the harmonic space reconstruction algorithms using well-conditioned image constraints.

In some such embodiments, the imaging agent consists of interacting superparamagnetic iron oxide (SPIO) or other, safe magnetic nanoparticles with surface-to-surface separation averaging less than 100 nm. This tight separation could easily exceed the safe allowable concentrations for humans or animals (e.g., under a few millimolar concentration, see Ferumoxytol FDA study 2010). To achieve high local concentration with safe systemic concentration, some embodiments use a carrier formulation of highly concentrated SPIOs. Here, the imaging nanoparticle agents are concentrated within a carrier (e.g., an oil-water emulsion, a liposome, a micelle, a PRINT nanoparticle carrier, a tethered "string of pearls", etc.). This carrier allows for high concentration of the nanoparticles within the carrier, while simultaneously maintaining a safe systemic concentration in the animal or human patient. It must also allow for individual SPIOs to aggregate quickly into a chain, which is crucial for the high SNR and high spatial resolution of strongly interacting MPI.

In some such embodiments, the imaging agent consists of nanoparticles of magnetic core diameter 15-35 nm. In other such embodiments, the imaging agent consists of nanoparticles of magnetic core diameter 35-60 nm.

In some such embodiments, the liquid inside the carrier is of low viscosity 0.1-1.0 cP to allow for chain formation of the SPIOs. In other such embodiments, the liquid inside the carrier is of medium viscosity 1.0-20.0 cP.

In some such embodiments, the imaging agent consists of interacting magnetic nanoparticles with surface-to-surface separation of <20 nm. In other such embodiments, the imaging agent consists of elongated magnetic cylinders with length >3×diameter.

In some embodiments, interacting magnetic nanoparticles are dispersed in high concentrations within an organic medium within a hydrophilic shell (larger encapsulating nanoparticle). The concentrations of the larger encapsulating nanoparticles are lower than the local concentration within the shell.

In some embodiments, interacting magnetic nanoparticles embedded within a solid matrix but with inter-particle distances as described above. In other such embodiments, interacting magnetic nanoparticles embedded on a lithographically etched disk/wafer (analogous to magnetic disk drives) but with inter-particle distances as described above.

A Magnetic Particle Imaging (MPI) agent together with a modified Magnetic Particle Imaging system is disclosed. Implementations may include a magnet configured to generate a magnetic field having a field-free line within the magnetic field, the field-free line having an axis and a center. A flux return may be integrated with the magnet configured such that a first magnetic flux path at approximately the center of the field-free line has a first reluctance and a second magnetic flux path distal from the center of the field-free line has a second reluctance, and the second reluctance is lower than the first reluctance.

In some variations, the imaging agent consists of interacting magnetic nanoparticles that can form approximately linear chains when immersed into an external magnetic field, where the inter-particle surface-to-surface separation distance is smaller than 100 nm.

In other variations, the imaging agent consists of interacting magnetic that can form approximately linear chains when immersed in a magnetic field, where the with inter-particle surface-to-surface separation distance is smaller than 20 nm.

In yet other variations, the imaging agent consists of elongated magnetic cylinder with length >3×diameter.

In other variations, where the imaging agent consists of interacting magnetic nanoparticles dispersed in an organic medium within a hydrophilic shell. Implementations of this variation can include surfactant-stabilized emulsion, shaken emulsion, dispersion, etc.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also contemplated that may include one or more processors and one or more memories coupled to the one or more processors. A memory, which can include a computer-readable storage medium, may include, encode, store, or the like, one or more programs that cause one or more processors to perform one or more of the operations described herein. Computer implemented methods consistent with one or more implementations of the current subject matter can be implemented by one or more data processors residing in a single computing system or across multiple computing systems. Such multiple computing systems can be connected and can exchange data and/or commands or other instructions or the like via one or more connections, including but not limited to a connection over a network (e.g., the interne, a wireless wide area network, a local area network, a wide area network, a wired network, or the like), via a direct connection between one or more of the multiple computing systems, etc.

We claim:

1. A strongly-interacting magnetic particle imaging system, comprising:
    a magnetic field generating system comprising at least one magnet, the magnetic field generating system providing:
        a gradient magnetic field within an observation region of the magnetic particle imaging system such that the gradient magnetic field will have a dynamic field-free region (FFR) for an object under observation having strongly-interacting magnetic particles distributed therein; and
        a drive field plus a slow shift field that dynamically shifts the FFR across a field of view (FOV) or partial FOV (pFOV) within the observation region, where a trajectory of the drive field accommodates for a coercivity of the strongly-interacting magnetic particles by ensuring that the strongly-interacting magnetic particles in the FOV or pFOV are saturated to a full coercivity field substantially immediately prior to traversing to an opposite-polarity of coercivity;
    a detection system arranged proximate the observation region, the detection system being configured to detect an induction signal from the strongly-interacting magnetic particles to provide a detection signal; and
    a signal processor in communication with the detection system, wherein the processor is configured to:
        receive the detection signal from the detection system;
        process the detection signal to remove a coercivity shift due to the coercivity of the strongly-interacting magnetic particles; and
        convert the processed detection signal into an image of the strongly-interacting magnetic particles.

2. The strongly-interacting magnetic particle imaging system of claim 1, wherein the drive field is a periodic drive field that has an amplitude that is sufficient to exceed the coercivity of the strongly-interacting magnetic particles, thereby ensuring that the strongly interacting particles are fully saturated prior to each traversal of the FFR.

3. The strongly-interacting magnetic particle imaging system of claim 1, wherein the signal processor is configured to process the detection signal using an x-space reconstruction method in one or more dimensions, including DC recovery over each partial FOV using a spatial continuity algorithm.

4. The strongly-interacting magnetic particle imaging system of claim 1, wherein the pulse sequence or acquisition trajectory and/or reconstruction method is configured to detect both conventional magnetic particle imaging signals and strongly-interacting magnetic particle imaging signals simultaneously.

5. The strongly-interacting magnetic particle imaging system of claim 1, wherein the system is frequency-flexible and amplitude-flexible to accommodate a range of coercive thresholds, chain formation, or chain crumble time constants, from a range of tracer/nanoparticles designs or from in vivo changes to the nanoparticles.

6. The strongly-interacting magnetic particle imaging system of claim 3, wherein the x-space reconstruction method in one or more dimensions further includes 1D, 2D, or 3D equalization or similar high pass filtering algorithms to curtail point spread function tails.

7. The strongly-interacting magnetic particle imaging system of claim 1, wherein the signal processor is configured to process the detection signal using a system matrix in one or more dimensions.

8. The strongly-interacting magnetic particle imaging system of claim 1, wherein the drive field accommodates for the coercivity of the strongly-interacting magnetic particles by exceeding a coercivity threshold before substantially immediately traversing to an opposite-polarity coercivity threshold, without stopping progress in the scan direction.

9. The strongly-interacting magnetic particle imaging system of claim 8, wherein the drive field traverses from a first coercivity threshold to the opposite-polarity coercivity threshold within 10 ms of exceeding the first coercivity threshold for every pixel in the image.

10. The strongly-interacting magnetic particle imaging system of claim 8, wherein the drive field shifts the FFR across the entire FOV or pFOV in a sinusoidal or linear raster scan pattern.

11. The strongly-interacting magnetic particle imaging system of claim 1, wherein the drive field accommodates for the coercivity of the strongly magnetic particles by shifting the FFR outside of the FOV in every dimension by a field that exceeds the coercivity threshold, before changing direction to scan the reverse direction of the shifting of the FFR.

12. The strongly-interacting magnetic particle imaging system of claim 1, wherein the drive field or other excitation components are configured to actively breakdown the strongly-interacting magnetic particle imaging tracers from their chain configuration to suppress siMPI detection signal and thereby provide biochemical or physiologic contrast.

13. The strongly-interacting magnetic particle imaging system of claim 1, wherein the gradient magnetic field is a dynamic gradient magnetic field.

14. The strongly-interacting magnetic particle imaging system of claim 1, wherein the gradient magnetic field is a static gradient magnetic field.

15. A strongly-interacting magnetic particle tracer, comprising:
a plurality of superparamagnetic nanoparticles, wherein the plurality of superparamagnetic particles are arranged to have a surface-to-surface separation between nearest-neighbor particles that does not exceed ten times a radius of the particles, and
wherein, in the presence of an applied magnetic field whose amplitude exceeds a coercivity threshold, the plurality of superparamagnetic nanoparticle manifests a measureable level of coercivity.

16. The strongly-interacting magnetic particle tracer of claim 15, wherein in the presence of the applied magnetic field whose amplitude exceeds the coercivity threshold, the plurality of superparamagnetic nanoparticle manifests a coercivity exceeding 0.1 mT.

17. The strongly-interacting magnetic particle tracer of claim 15, wherein, in the presence of an applied magnetic field, the superparamagnetic nanoparticles form chains.

18. The strongly-interacting magnetic particle tracer of claim 17, wherein the chains comprise five to 100 superparamagnetic nanoparticles.

19. The strongly-interacting magnetic particle tracer of claim 17, wherein the chains comprise 100 to 500 superparamagnetic nanoparticles.

20. A method of strongly-interacting magnetic particle imaging, comprising:
placing strongly-interacting magnetic particles into an observation region;
generating within the observation region an inhomogeneous magnetic field having a spatial gradient and having a field-free region (FFR) within the imaging region;
generating within the observation region a drive field that dynamically shifts the FFR across a field of view (FOV) within the observation region while accommodating for a coercivity of the strongly-interacting magnetic particles;
detecting signals produced by the strongly-interacting magnetic particles in the observation region; and
producing from the detected signals an image of the strongly-interacting magnetic particles in the observation region,
wherein the producing the image includes processing the detected signals to remove a coercivity shift due to a coercivity of the strongly-interacting magnetic particles.

* * * * *